United States Patent
Sheriff et al.

(10) Patent No.: US 12,211,625 B2
(45) Date of Patent: Jan. 28, 2025

(54) SYSTEMS AND METHODS FOR DETECTING AND TRACKING INFECTIOUS DISEASES USING SENSOR DATA

(71) Applicant: Cisco Technology, Inc., San Jose, CA (US)

(72) Inventors: Akram Ismail Sheriff, San Jose, CA (US); Hazim Hashim Dahir, Wake Forest, NC (US); Thomas Szigeti, Vancouver (CA)

(73) Assignee: Cisco Technology, Inc., San Jose, CA (US)

( * ) Notice: Subject to any disclaimer, the term of this patent is extended or adjusted under 35 U.S.C. 154(b) by 629 days.

(21) Appl. No.: 17/169,392

(22) Filed: Feb. 5, 2021

(65) Prior Publication Data
US 2022/0254509 A1   Aug. 11, 2022

(51) Int. Cl.
| | | |
|---|---|---|
| G16H 50/80 | (2018.01) | |
| F24F 11/30 | (2018.01) | |
| G16H 10/60 | (2018.01) | |
| G16H 15/00 | (2018.01) | |
| G16H 40/20 | (2018.01) | |
| G16H 40/67 | (2018.01) | |
| G16H 80/00 | (2018.01) | |

(52) U.S. Cl.
CPC .............. *G16H 50/80* (2018.01); *F24F 11/30* (2018.01); *G16H 10/60* (2018.01); *G16H 15/00* (2018.01); *G16H 40/20* (2018.01); *G16H 40/67* (2018.01); *G16H 80/00* (2018.01)

(58) Field of Classification Search
None
See application file for complete search history.

(56) References Cited

U.S. PATENT DOCUMENTS

| | | | | |
|---|---|---|---|---|
| 7,447,333 | B1 * | 11/2008 | Masticola | G16H 50/80 |
| | | | | 382/128 |
| 9,175,356 | B2 * | 11/2015 | Peltz | G16H 50/80 |
| 10,966,632 | B2 * | 4/2021 | Hijnen | A61M 16/161 |
| 11,342,051 | B1 * | 5/2022 | Jain | G16H 10/60 |
| 11,592,196 | B2 * | 2/2023 | Sims, Jr. | F24F 11/74 |
| 2006/0021375 | A1 * | 2/2006 | Wetzel | F24F 3/167 |
| | | | | 62/419 |

(Continued)

FOREIGN PATENT DOCUMENTS

| | | | | |
|---|---|---|---|---|
| WO | WO-2018080048 A1 * | 5/2018 | | A61B 5/00 |
| WO | WO2019038271 A1 | 2/2019 | | |

OTHER PUBLICATIONS

Bennett et. al., Military-grade camera shows risks of airborne coronavirus spread, Dec. 11, 2020, The Washington Post. (Year: 2020).*

(Continued)

*Primary Examiner* — Anne-Marie K Alderson
(74) *Attorney, Agent, or Firm* — Lee & Hayes, P.C.

(57) ABSTRACT

An example method for identifying and reporting a space or individual that has been exposed to an infectious disease includes identifying sensor data related to one or more individuals in a space; determining, based on the sensor data, that a particular individual among the one or more individuals is infected with an infectious disease; generating a report requesting that the space be disinfected; and outputting the report to a computing device.

14 Claims, 7 Drawing Sheets

(56) References Cited

U.S. PATENT DOCUMENTS

| | | | |
|---|---|---|---|
| 2009/0069642 A1* | 3/2009 | Gao | H04L 67/125 |
| | | | 600/300 |
| 2013/0013331 A1 | 1/2013 | Horseman | |
| 2013/0215245 A1* | 8/2013 | Haidegger | G08B 21/24 |
| | | | 348/77 |
| 2014/0278220 A1* | 9/2014 | Yuen | A61B 5/681 |
| | | | 702/150 |
| 2014/0333744 A1* | 11/2014 | Baym | G08B 21/245 |
| | | | 348/77 |
| 2015/0094097 A1 | 4/2015 | Fraccaroli | |
| 2016/0313017 A1* | 10/2016 | Nauls | F24F 11/77 |
| 2017/0018007 A1 | 1/2017 | DeFrank et al. | |
| 2017/0173262 A1* | 6/2017 | Veltz | G16H 20/17 |
| 2017/0219231 A1* | 8/2017 | Hui | F24F 11/76 |
| 2017/0367651 A1* | 12/2017 | Tzvieli | A61B 5/0075 |
| 2018/0049669 A1* | 2/2018 | Vu | A61B 5/0507 |
| 2019/0088373 A1* | 3/2019 | Sarmentero | G16H 40/67 |
| 2019/0159951 A1* | 5/2019 | Hadley | A47K 1/00 |
| 2019/0209046 A1* | 7/2019 | Addison | G06T 7/0014 |
| 2020/0043318 A1 | 2/2020 | Laufer et al. | |
| 2020/0138292 A1* | 5/2020 | Choi | A61B 5/091 |
| 2020/0176125 A1* | 6/2020 | Chatterjea | G16H 40/20 |
| 2020/0227160 A1* | 7/2020 | Youngblood | G16H 40/67 |
| 2020/0304944 A1 | 9/2020 | Millius et al. | |
| 2020/0348038 A1* | 11/2020 | Risbeck | F24F 11/70 |
| 2020/0393159 A1 | 12/2020 | Takayanagi | |
| 2021/0010701 A1* | 1/2021 | Nesler | F24F 3/14 |
| 2021/0074436 A1* | 3/2021 | Trim | A47L 9/2852 |
| 2021/0243081 A1* | 8/2021 | Pal | A61B 5/7435 |
| 2021/0272702 A1* | 9/2021 | Hakami | H04W 4/027 |
| 2021/0319909 A1* | 10/2021 | Grissen | G16H 40/67 |
| 2021/0353897 A1* | 11/2021 | Wang | A61M 16/009 |
| 2021/0358068 A1* | 11/2021 | Boszczyk | G06Q 50/265 |
| 2021/0373519 A1* | 12/2021 | Risbeck | F24F 11/47 |
| 2021/0393834 A1* | 12/2021 | Wellig | F24F 11/63 |
| 2022/0031161 A1* | 2/2022 | Marathe | A61B 5/0008 |
| 2022/0034526 A1* | 2/2022 | Sims, Jr. | F24F 9/00 |
| 2022/0034542 A1* | 2/2022 | Peters | F24F 11/0001 |
| 2022/0101290 A1* | 3/2022 | Handshaw | G16H 40/63 |
| 2022/0203808 A1* | 6/2022 | Carr | B60H 1/00371 |

OTHER PUBLICATIONS

Solinski, et al., "Automatic Cough Detection Based on Airflow Signals for Portable Spirometry System," Informatics in Medicine Unlocked, vol. 18, Mar. 2020, pp. 1-18.

The Invitation to Pay Additional Fees for PCT Application No. PCT/US22/15359, mailed May 16, 2022, 15 pages.

The International Search Report and Written Opinion for PCT Application No. PCT/US22/15359, mailed Jul. 11, 2022, 17 pages.

Skodova, et al., "Hand hygiene assessment in the workplace using a UV lamp," AJIC: American Journal of Infection Control, Elsevier, Amsterdam, NL, Vol. 43, No. 12, Aug. 18, 2015 (Aug. 18, 2015), pp. 1360-1362, XP029327014, ISSN: 0196-6553, DOI: 10.1016/J.AJIC.2015.07.003 the whole document.

* cited by examiner

SYSTEMS AND METHODS FOR DETECTING AND TRACKING INFECTIOUS DISEASES USING SENSOR DATA

TECHNICAL FIELD

The present disclosure relates generally to techniques for predicting whether a first individual has an infectious disease, identifying spaces exposed to the infectious disease, and identifying second individuals exposed to the infectious disease. The present disclosure also relates to reporting various events associated with the infectious disease.

BACKGROUND

Infectious diseases represent serious threats to human health. For example, in 2020, a global pandemic caused by an outbreak of coronavirus disease 19 (COVID-19) was believed to be responsible for millions of deaths, globally. Those who contract COVID-19 often remain affected for months after recovery. For example, an individual exhibiting long COVID may experience shortness of breath, chest palpitations, chest pain, headaches, insomnia, and psychological disorders, such as depression, for months after recovering from their initial COVID-19 infection.

Infectious diseases can also cause significant economic harm. For example, because severe acute respiratory syndrome coronavirus 2 (SARS-CoV-2) (the infectious agent responsible for COVID-19 infections) is thought to be transmissible by droplets and/or aerosols in the air, governments and businesses have closed shared spaces to the public and/or employees to prevent the spread of COVID-19. For businesses that rely on collaboration between employees in shared, physical workspaces and/or businesses that rely on customers being present in public spaces, these closures have significantly disrupted operations.

Public health agencies and private businesses use contact tracing to identify the spread of infectious diseases in various communities. However, many current contact tracing techniques are inaccurate, slow, or otherwise ineffective for preventing the spread of infectious diseases. For example, many contact tracing mechanisms rely on individuals self-reporting their symptoms and/or diagnoses of infectious diseases, many of whom may forget or refuse to disclose their disease statuses. Furthermore, automated contact tracing tools often rely on mobile connectivity of devices associated with various individuals within the monitored population. These tools are ineffective for individuals in areas without mobile connectivity, for individuals who have rejected participation in these tools (e.g., out of privacy concerns), and for individuals who do not have devices with mobile wireless connectivity.

BRIEF DESCRIPTION OF THE DRAWINGS

The detailed description is set forth below with reference to the accompanying figures. In the figures, the left-most digit(s) of a reference number identifies the figure in which the reference number first appears. The use of the same reference numbers in different figures indicates similar or identical items. The systems depicted in the accompanying figures are not to scale and components within the figures may be depicted not to scale with each other.

DESCRIPTION OF EXAMPLE EMBODIMENTS

Overview

Figure 1:
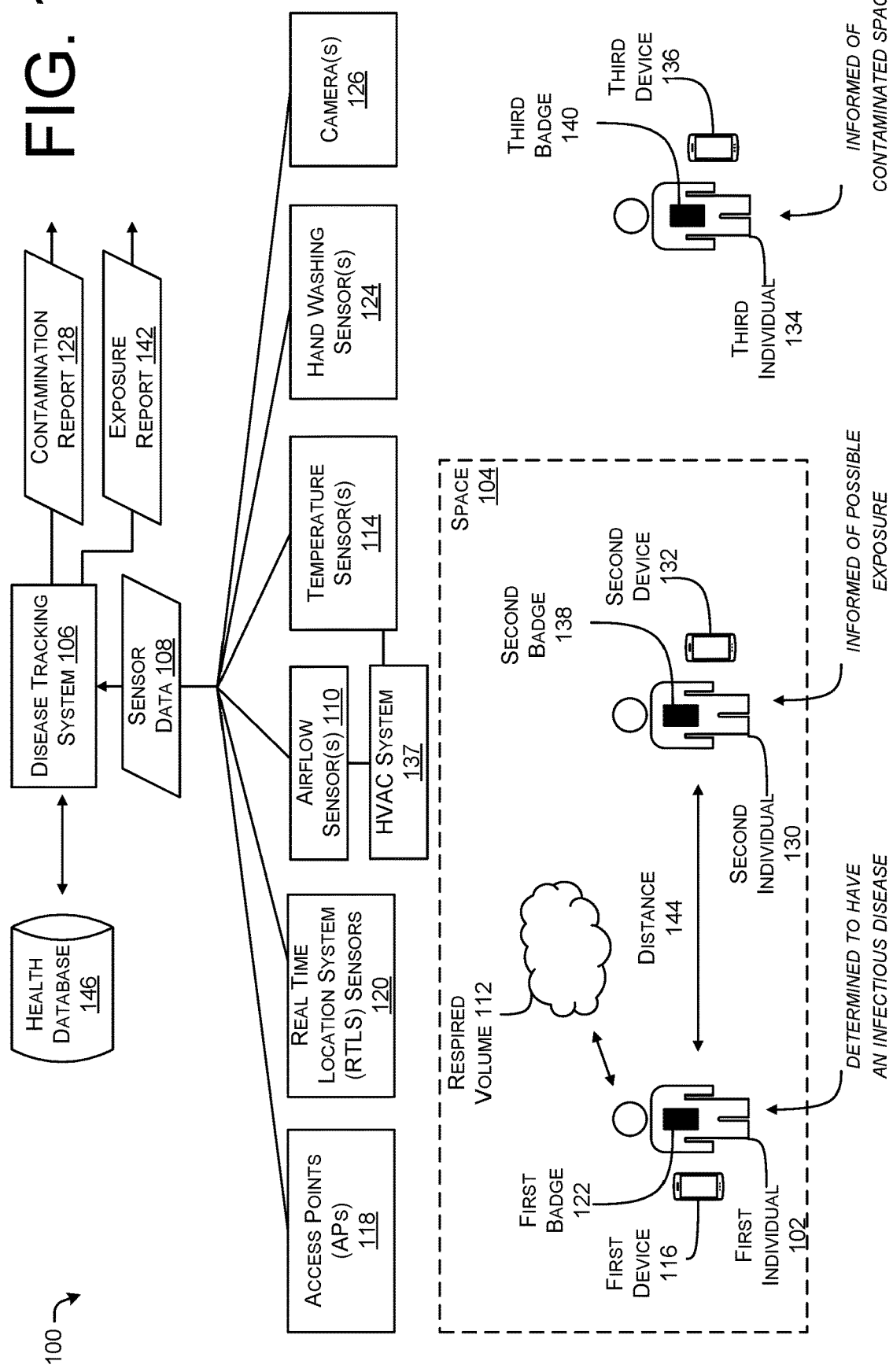
FIG. 1 illustrates an example environment or predicting and tracking exposure of an infectious disease.

This disclosure describes various techniques for identifying people and spaces exposed to an infectious disease. An example method includes identifying sensor data related to one or more individuals in a space, determining, based on the sensor data, that a particular individual among the one or more individuals is infected with an infectious disease; generating a report requesting that the space be disinfected; and outputting the report to a computing device.

In some examples, identifying the sensor data comprises detecting, by one or more infrared cameras, a surface temperature or a core temperature of the particular individual. In some instances, determining based on the sensor data, that the particular individual is infected with the infectious disease comprises determining that the surface temperature or the core temperature is greater than a threshold temperature.

In various examples, identifying the sensor data comprises detecting, by one or more infrared cameras, a volume of air inhaled or exhaled by the particular individual. In some cases, determining, based on the sensor data, that the particular individual is infected with the infectious disease comprises at least one of: determining, based on the volume of air, that the particular individual has sneezed or coughed; or determining that the volume of air is less than a threshold volume.

In various implementations, the method includes capturing, by one or more cameras and within a threshold time period of the particular individual washing a hand of the particular individual, at least one image of the hand of the particular individual illuminated with an ultraviolet (UV) light; and determining that the at least one image depicts greater than a threshold amount of particles on a surface of the hand.

According to some examples, the sensor data being first sensor data, the space being a particular space among multiple spaces, the method further comprising: identifying second sensor data indicative of a location of the particular individual in the multiple spaces during a time interval; and determining, based on the second sensor data, that a dwell time of the particular individual in the particular space is greater than a threshold. In particular cases, identifying the second sensor data indicative of the location of the particular individual during the time interval comprises: detecting, by a real time location system (RTLS), a position of an RTLS tag attached to a badge carried by the particular individual. In various examples, the computing device being a first computing device, wherein identifying the second sensor data indicative of the location of the particular individual during the time interval comprises: detecting, by one or more access points (APs), that a second device associated with the particular individual has exchanged data wirelessly with the one or more APs; and determining the location of the particular individual based on one or more locations of the one or more APs.

An example method includes identifying first sensor data indicative of a first badge associated with a first individual being at a first location for greater than a threshold time period; identifying second sensor data indicative of a second badge associated with a second individual being at a second location; determining that the first individual is infected with an infectious disease; determining, based on the first sensor data and the second sensor data, that the first location was within a threshold distance of the second location; generating a report indicating that the second individual has been exposed to the infectious disease; and transmitting, to a computing device associated with the second individual, the report. For instance, a real time location system (RTLS) sensor is configured to: generate the first sensor data by at least one of transmitting or receiving a first wireless signal with a first RTLS tag attached to the first badge; and generate the second sensor data by at least one of transmitting or receiving a second wireless signal with a second RTLS tag attached to the second badge.

In some cases, one or more infrared sensors are configured to detect a temperature of the first individual. For instance, determining that the first individual is infected with an infectious disease comprises determining that the temperature is greater than a threshold temperature.

In particular examples, one or more infrared cameras are configured to detect a volume of air inhaled or exhaled by the first individual. In particular cases, determining that the first individual is infected with the infectious disease is based on the volume of the air. For instance, determining, based on the first sensor data and the second sensor data, that the first location was within the threshold distance of the second location comprises determining, based on the volume of the air, that the first individual sneezed or coughed within the threshold distance of the second location.

The example method may further include transmitting, to a heating, ventilation, and air conditioning (HVAC) system, an instruction to increase airflow at the second location.

In some cases, the computing device is a first computing device, the second sensor data is further indicative of a third location of the first computing device, and the first sensor data is further indicative of third location of a second computing device associated with the first individual. For instance, the first sensor data comprises connectivity data indicative of one or more access points (APs) that have at least one of transmitted or received data wirelessly with the second computing device.

According to various implementations, wherein the infectious disease comprises a viral infection, a fungal infection, a parasitic infection, or a bacterial infection.

Particular implementations also relate to systems and devices configured to perform any of the functions described herein.

EXAMPLE EMBODIMENTS

This disclosure describes various techniques for detecting that an individual has an infectious disease, and identifying spaces and/or other individuals exposed to the infectious disease. In some cases, a report requesting that the exposed spaces be disinfected is generated and transmitted to an external computing device. In some implementations, a report requesting that the exposed spaces be avoided is generated and transmitted to an external computing device. In particular examples, a report informing the infected individual of the infectious disease is generated and transmitted to an external computing device. In particular implementations, a report informing another individual of the exposure to the infectious disease is generated and transmitted to an external computing device.

Implementations of the present disclosure are directed to various improvements in the technical field of contact tracing. In particular cases, sensors can monitor multiple individuals in a space (e.g., an office building) simultaneously without contacting those individuals. Accordingly, the systems can more efficiently monitor individuals for symptoms of an infectious disease, simultaneously than other techniques requiring personalized health monitors for the individuals. In various examples described herein, the individuals can be monitored without microphones monitoring sounds from the individuals, thereby substantially maintaining the privacy of the individuals within the space. Further, in some cases, the individuals can be monitored without monitoring the locations of devices (e.g., mobile phones) associated with the individuals, which can further enhance the privacy of the individuals. In various examples, individuals can be tracked without exposing the identities of the individuals. In various implementations, reports indicating that a space and/or individual has been exposed to an infectious disease without indicating the identity of the individual that was the source of the infectious disease, thereby maintaining privacy.

Various implementations of the present disclosure will be described in detail with reference to the drawings, wherein like reference numerals present like parts and assemblies throughout the several views. Additionally, any samples set forth in this specification are not intended to be limiting and merely demonstrate some of the many possible implementations.

FIG. 1 illustrates an example environment 100 for predicting and tracking exposure of an infectious disease. As shown in FIG. 1, a first individual 102 is located in a space 104. The first individual 102, for example, is a human being or another type of animal. In some examples, the first individual 102 is a patient, an employee of an enterprise, a subject, or the like. The space 104, in various implementations, is a room, hallway, warehouse, building, vehicle (e.g., an ambulance), temporary structure (e.g., a tent), or another type of enclosed space. As used herein, the term "enclosed space," and its equivalents, can refer to a volume that is bounded by multiple walls, such as vertical walls, a ceiling, and/or a floor.

In various implementations, the first individual 102 may be infected with an infectious disease. As used herein, the term "infectious disease," and its equivalents, can refer to a disorder caused by an infectious agent (e.g., bacteria, viruses, fungi, parasites, or a combination thereof). Examples of the infectious disease include coronavirus-based infections, such as middle east respiratory syndrome (MERS), severe acute respiratory syndrome (SARS), and coronavirus disease 19 (COVID-19); *Corynebacterium*-based infections, such as diptheria; ebolavirus-based infections, such as ebola; orthomyxoviridae virus-based infections, such as influenza A, B, or C; hepatovirus A, B, C, D, or E-based infections, such as hepatitis; *Haemophilus*-based infections, such as hib disease; human immunodeficiency virus (HIV)-based infections, such as acquired immunodeficiency syndrome (AIDS); human papillomavirus (HPV)-based infections; Morbillivirus-based infections, such as measles; *Mycobacterium*-based infections, such as tuberculosis; *Neisseria*-based infections, such as meningitis; Orthorubulavirus-based infections, such as mumps; norovirus-based infections; *Streptococcus*-based infections; enterovirus-based infections, such as polio; Orthopneumovirus-based infections; rotavirus-based infections; Rubivirus-based infections, such as rubella; herpesvirus-based infections, such as chickenpox or shingles; *Clostridium*-based infections, such as tetanus or botulism; Bordatella-based infections, such as pertussis; Flavivirus-based infections, such as Zika; and so on.

Once infected, the first individual 102 may experience symptoms associated with the infectious disease. In various cases, the first individual 102 may experience symptoms associated with an immune response to the infectious agent, which may be a reaction resulting from the immune system of the first individual 102 defending against or destroying the infectious agent. For example, the first individual 102 may experience a core body temperature (also referred to as a "core temperature") of greater than 37.5° Celsius (also referred to as a "fever"), which may make the body of the first individual 102 less hospitable to the infectious agent. In some instances, the first individual 102 may experience inflammation in the respiratory tract, which may cause the first individual 102 to cough or may inhale or exhale a reduced respiratory volume. In particular examples, the first individual 102 may experience irritation in the respiratory epithelium lining of the nose (e.g., due to the release of histamine by immune cells in the nasal mucosa), which may cause the first individual 102 to sneeze. Other examples of symptoms of the infectious disease could include a rash, fatigue, runny nose, sore throat, a low core body temperature, vomiting, or the like. An example infectious disease may be associated with one or more particular symptoms.

According to implementations of the present disclosure, a disease tracking system 106 may be configured to predict whether the first individual 102 is infected with an infectious disease based on sensor data 108 generated by one or more sensors. The disease tracking system 106 may be implemented in hardware, software, or a combination thereof. In some cases, the disease tracking system 106 is implemented in a cloud-based network, a mesh network, or the like. In some examples, the disease tracking system 106 may be implemented by a system configured to implement a location and/or internet of things (IoT)-as-a-service platform, which may be connected to various devices (e.g., IoT devices, sensors, etc.) within an environment and may be used to track and monitor assets. In some cases, the disease tracking system 106 may receive the sensor data 108 data from the devices, analyze the sensor data 108, and present the results of the analysis to one or more administrators of the environment 100.

In various implementations, the disease tracking system 106 may process the sensor data 108. For instance, the disease tracking system 106 may include one or more analog and/or digital filters configured to remove noise and/or artifact from the sensor data 108. Examples of noise that the disease tracking system 106 is configured to remove from the sensor data 108 include white noise, pink noise, Brownian noise, Gaussian noise, image noise (e.g., shadow noise, speckle noise, etc.), and so on. The disease tracking system 106, for example, may include one or more of a band-pass filter, a band-reject filter, Bessel filter, a biquad filter, a Butterworth filter, a Chebyshev filter, an Elliptical filter, a high-pass filter, a Kalman filter, or a low-pass filter. The disease tracking system 106 may perform other signal processing techniques known to those having skill in the art.

In various examples, the environment 100 includes one or more airflow sensors 110 in communication with the disease tracking system 106. In various examples, the airflow sensor(s) 110 are configured to detect airflow around the first individual 102 without contacting the first individual 102. That is, the airflow sensor(s) 110 may be "noncontact sensor(s)." In particular examples, the airflow sensor(s) 110 are configured to detect a respired volume 112 in the space 104. The respired volume 112 is a volume of air that is inhaled and/or exhaled by the first individual 102. According to various examples, the airflow sensor(s) 110 includes an infrared sensor (e.g., an infrared camera) configured to detect the respired volume 112 at one or more times. For instance, if the respired volume 112 is exhaled by the first individual 102, the temperature (and therefore infrared emission) of the respired volume 112 may be greater than an ambient temperature in the space 104. The airflow sensor(s) 110 may therefore detect the respired volume 112 based on the difference between the temperature of the respired volume 112 and the ambient air within the space 104. In some cases, the airflow sensor(s) 110 are configured to detect at least one of a volume, a motion (e.g., a speed or velocity), or a turbulence of the respired volume 112. The airflow sensor(s) 110 may indicate the volume, motion, and/or turbulence (e.g., the presence of vortices) of the respired volume 112 in the sensor data 108 and may transmit the sensor data 108 to the disease tracking system 106. In particular examples, the airflow sensor(s) 110 include an infrared camera, such as I-SEE™ by Mitsubishi Electric of Tokyo, Japan.

In various examples, the disease tracking system 106 may predict whether the first individual 102 is infected with the infectious disease based on the volume, motion, and/or turbulence of the respired volume 112 indicated in the sensor data 108. In some examples, the disease tracking system 106 may predict that the first individual 102 is infected based on determining that the volume of the respired volume 112 is below a threshold volume, which may indicate that the first individual 102 has a swollen respiratory tract, pneumonia, or some other symptom associated with decreased respiratory function.

In particular cases, the disease tracking system 106 may predict that the first individual 102 is infected by detecting that the first individual 102 has coughed or sneezed based on the volume, motion, and/or turbulence of the respired volume 112. For instance, the disease tracking system 106 may determine that the first individual 102 has coughed or sneezed based on determining that the volume of the respired volume 112 is above a threshold volume, determining that a speed or velocity of the respired volume 112 is above a threshold speed or velocity, or determining that the respired volume 112 is substantially turbulent (e.g., the respired volume 112 includes one or more vortices). In some cases, the disease tracking system 106 may predict that the first individual 102 is infected based on determining that the first individual 102 has coughed or sneezed greater than a threshold number of times (e.g., within a particular time period), determining that a rate of sneezing or coughing by the first individual 102 has increased greater than a threshold amount, or the like. In various implementations, a cough or sneeze by the first individual 102 may be detected without the use of a microphone monitoring the first individual 102, thereby providing enhanced privacy to the first individual 102 over systems that perform cough or sneeze detection based on audio signals.

According to various implementations, the environment 100 includes one or more temperature sensors 114 in communication with the disease tracking system 106. In various examples, the temperature sensor(s) 114 are configured to detect a temperature of the first individual 102 without contacting the first individual 102. That is, the temperature sensor(s) 114 may be "noncontact sensor(s)." In particular examples, the temperature sensor(s) 114 are configured to detect a surface temperature of the first individual 102. For example, the temperature sensor(s) 114 may include an infrared sensor (e.g., an I-SEE™ sensor) configured to detect a temperature of a surface of the first individual 102, such as a temperature of a forehead of the first individual 102, a temperature within a nostril of the first individual 102, a temperature within a mouth of the first individual 102 (e.g., while the first individual 102 is speaking or yawning), or the like. In some cases, the temperature sensor(s) 114 may be configured to determine a core temperature of the first individual 102 based on the surface temperature. For example, the temperature sensor(s) 114 may store a model indicating a correlation between the surface temperature and the core temperature. The temperature sensor(s) 114 may indicate the temperature (e.g., the surface temperature, the core temperature, or a combination thereof) of the first individual 102 in the sensor data 108 and may transmit the sensor data 108 to the disease tracking system 106.

In particular cases, the disease tracking system 106 may predict that the first individual 102 is infected by detecting that the temperature (e.g., the surface temperature or the core temperature) of the first individual 102 is outside of a particular range. The disease tracking system 106 may determine that the temperature is lower than a first temperature threshold or that the temperature is greater than a second temperature threshold. The second temperature threshold, for instance, may be greater than or equal to 36.0° C. and less than or equal to 36.5° C. In various cases, the second temperature threshold may be greater than or equal to 37.2° C. and less than or equal to 38.5° C. For instance, the first temperature threshold may be 36.3° C. and the second temperature threshold may be 37.7° C. In some cases, the first temperature threshold and the second temperature threshold change over time. For example, the second temperature threshold may be relatively higher during the afternoon and relatively lower during the morning.

According to various examples, the disease tracking system 106 may determine that the first individual 102 is infected based on multiple factors, which may reduce the risk of incorrectly determining that the first individual 102 is infected. For example, the disease tracking system 106 may determine that the first individual 102 is infected based on the volume of the respired volume 112. However, to confirm that the first individual is not merely experiencing seasonal allergies, the disease tracking system 106 may also confirm that the temperature of the first individual 102 is outside of the particular range. Thus, by considering these multiple factors, the disease tracking system 106 can increase the accuracy of determining that the first individual 102 is infected.

In particular implementations, the disease tracking system 106 may determine the type of infectious disease exhibited by the first individual 102. The disease tracking system 106 may store a computing model that correlates one or more symptoms to a particular type of infectious disease and/or infectious agent. For example, the disease tracking system 106 may determine, using the computing model, that a feature (e.g., volume and/or velocity) of the respired volume 112 and/or temperature of the first individual 102 is indicative of COVID-19 infection.

In some examples, the disease tracking system 106 may determine that the first individual 102 is infected based on data transmitted from an external device. For instance, the first individual 102 may be associated with a first device 116, which can be a computing device. As used herein, the terms "computing device," "electronic device," "computer," and their equivalents can refer to any device including hardware that is configured to execute software. Examples of computing devices include mobile phones, tablet computers, personal computers, laptops, smart televisions, servers, certain IoT devices, and the like. The first individual 102 may self-report the infectious disease based on an experience of the first individual 102, such as based on a visit with a health-care provider or experience of symptoms associated with the infectious disease. The first individual 102 may enter an indication of the infectious disease into the first device 116 (or some other computing device). The first device 116 may transmit an indication of the infectious disease to the disease tracking system 106. Based on the indication of the infectious disease, the disease tracking system 106 may determine that the first individual 102 is infectious. In some examples, the first device 116 executes an application that facilitates self-reporting of the infectious disease by the first individual 102.

In various cases, the infectious agent is transmissible to and from the first individual 102. For example, the infectious agent may have been transferred from another individual to the first individual 102. Similarly, the infectious agent may be capable of being transferred from the first individual 102 to another individual. In some cases, the infectious agent is transmitted via fomites. For example, influenzavirus A (a type of Orthornavirus) can be transmitted by touching the surfaces of doorknobs, buttons, or furniture that were previously touched by an infected individual. In various implementations, the infectious agent is transmitted via aerosols and/or droplets transmitted through the air. For instance, SARS coronavirus 2 (SARS-CoV-2) is believed to be transmitted by inhaling aerosols and/or droplets exhaled by an infected individual. Infectious agents transmitted via aerosols and/or droplets can be particularly transmissible in enclosed spaces.

The disease tracking system 106 may identify that the first individual 102 has exposed the space 104 to the infectious disease based on determining that a location of the first individual 102 is within the space 104. The disease tracking system 106 may determine the location of the first individual 102 based on location sensors within the space 104.

The environment 100 may include access points (APs) 118 configured to exchange (e.g., transmit or receive) wireless signals (also referred to as "connectivity data" or "connectivity signals") with the first device 116. The wireless signals, for example, are radio frequency wireless signals, such as BLUETOOTH™ signals, WI-FI™ signals, radio signals (e.g., wireless signals utilized by one or more radio access networks (RANs), such as $3^{rd}$ Generation Partnership Project (3GPP) RANs), or the like. In general, the first device 116 may be carried by the first individual 102, attached to the first individual 102, or within the vicinity of the first individual 102. Thus, the location of the first device 116 may correlate to the location of the first individual 102. The APs 118 may be located in predetermined positions, such that a range of transmissions received by the APs 118 originate from locations within the space 104 and/or that a range or transmissions by the APs 118 terminate in locations within the space 104. The APs 118 may determine that the first device 116 is located in the space 104 by receiving at least one transmission from the first device 116 and/or by determining that at least one transmission from the APs 118 was successfully received by the first device 116. According to some implementations, the APs 118 may calculate a round-trip-time (RTT) of wireless signals exchanged by the first device 116 and the APs 118 and may calculate the distance between the APs 118 and the first device 116 based on the RTT. For instance, the APs 118 may perform a ping operation with the first device 116. In some examples, the APs 118 determine that the first device 116 has exchanged wireless signals (e.g., has transmitted and/or received signals) from multiple APs 118 and/or may determine the distances between the first device 116 and multiple APs 118, and may find the location of the first device 116 using triangulation. According to some examples, the location of the first device 116 is determined based on an angle of arrival (AoA) of signals received by the APs 118 from the first device 116. In some cases, the first device 116 estimates its own location (e.g., using global positioning service (GPS) signals received from satellites) and self-reports its location to the APs 118 via one or more wireless signals. The APs 118 may indicate the location of the first device 116 in the sensor data 108. Thus, the disease tracking system 106 may track the location of the first individual 102 within the space 104.

In various implementations, the environment 100 may include real time location system (RTLS) sensors 120 in communication with the disease tracking system 106. The RTLS sensors 120 may be configured to identify a location of a first badge 122 associated with the first individual 102. The first badge 122, for example, may be an identification (ID) badge of the first individual 102 within the space 104, which could be a workplace of the first individual 102. In some examples, the first badge 122 may be an access badge of the first individual 102. For instance, a scanner may detect the first badge 122, validate the first badge 122, and may temporarily unlock or open a door such that the first individual 102 can access a restricted area within the space 104. The first badge 122 may include, or may be attached to, a tag that can be detected by the RTLS sensors 120. For example, the first badge 122 may broadcast a signal (e.g., a BLUETOOTH™ Low Energy (BLE) signal, a near field communication (NFC) signal, a WI-FI™ signal, or the like) that is detected by the RTLS sensors 120. The RTLS sensors 120 may determine the times at which the RTLS sensors 120 receive the signal from the first badge 122. Based on a difference between the times at which the RTLS sensors 120 receive the signal, and the positions of the receivers of the RTLS sensors 120, the RTLS sensors 120 may be configured to triangulate the position of the first badge 122. The RTLS sensors 120 may indicate the location of the first badge 122 in the sensor data 108. Notably, the disease tracking system 106 may track the location of the first individual 102 within the space 104 based on the sensor data 108 from the RTLS sensors 120 even if the first individual 102 is separated from the first device 116, the first device 116 is deactivated (e.g., powered off), the first individual 102 is positioned at a location wherein the first device 116 is unable to transmit and/or receive data wirelessly from the APs 118, or the like.

The disease tracking system 106 may determine that the first individual 102 has contaminated the space 104 with the infectious agent based on the presence of the infected first individual 102 within the space 104. In some examples, the disease tracking system 106 may track the location of the first individual 102 within the space 104 over time. For example, the disease tracking system 106 may receive the sensor data 108 repeatedly and/or periodically, which may indicate the location of the first individual 102 at multiple time points. In various cases, the disease tracking system 106 may determine a dwell time of the first individual 102 within the space 104. As used herein, the term "dwell time," and its equivalents, may refer to a time interval during which an individual continuously occupies a space and/or a location without leaving the space and/or location. The dwell time of the first individual 102 in the space 104 may be correlated to the likelihood that the first individual 102 has contaminated the space 104 with the infectious agent.

In various examples, the disease tracking system 106 may further track the potential of the first individual 102 for spreading the infectious disease in the space 104. The environment 100 may further include one or more hand washing sensors 124, which may also be communicatively coupled to the disease tracking system 106. In particular examples, the hand washing sensor(s) 124 are configured to detect an efficacy of hand washing of the first individual 102. For instance, the hand washing sensor(s) 124 may be located proximately to one or more sinks or thresholds (e.g., doorways) of bathrooms within the space 104. In various examples, the hand washing sensor(s) 124 include a light source, which may be an ultraviolet (UV) light source. The hand washing sensor(s) 124 may further include a sensor, such as a camera, configured to capture images of scenes illuminated by the light source. In particular instances, the hand washing sensor(s) 124 are configured to capture at least one illuminated image of the hands of the first individual 102 within a time period (e.g., 30 seconds) after the first individual 102 washes the hands. The hand washing sensor(s) 124 may be further configured to process the image(s) of the hands and detect particles on the hands. Based on an amount of the particles on the hands, the hand washing sensor(s) 124 may be configured to determine an efficacy of the hand washing performed by the first individual 102. The hand washing sensor(s) 124 may be configured to include an indication of the efficacy of the hand washing performed by the first individual 102 in the sensor data 108. Ineffective hand washing can lead to an increased chance of disease transmission, particularly for infectious diseases associated with fomite-based transmission. Thus, the disease tracking system 106 may determine a likelihood that the first individual 102 has contaminated the space 104 with the infectious agent based on the indication of the hand washing performed by the first individual 102.

In some examples, the environment 100 further includes one or more cameras 126 communicatively coupled to the disease tracking system 106. The camera(s) 126 may be configured to capture images (e.g., of the face) of the first individual 102 in the space 104 over time. In some cases, the camera(s) 126 may further process the images in order to identify whether the first individual 102 is wearing PPE, such as a face mask or gloves. The camera(s) 126 may include, in the sensor data 108, an indication of the images and/or whether the images depict the first individual 102 wearing PPE. Wearing PPE, such as face masks or gloves, can reduce the chance of disease transmission. In some cases, the disease tracking system 106 may determine a likelihood that the first individual 102 has contaminated the space 104 with the infectious agent based on whether the first individual 102 is wearing the PPE. In some cases, the camera(s) 126 may be further used to track the location of the first individual 102 using feature detection and/or computer vision techniques, and the location of the first individual 102 can be indicated in the sensor data 108.

The disease tracking system 106 may further determine whether the first individual 102 has contaminated the space 104 based on the type of infectious agent that has infected the first individual 102. For example, the disease tracking system 106 may identify a type of transmissibility of the infectious agent. If there is a relatively high risk that the infectious agent can be transmitted by fomites (e.g., the disease tracking system 106 determines that the first individual 102 is infected with an influenza), then the efficacy of the hand washing performed by the first individual 102 may be relatively significant to the overall likelihood that the first individual 102 has contaminated the space 104, or vice versa. If there is a relatively high risk that that the infectious agent can be transmitted by droplets and/or aerosols (e.g., the disease tracking system 106 determines that the first individual 102 is infected with a coronavirus), then the efficacy of the hand washing performed by the first individual 102 may be relatively significant to the overall likelihood that the first individual 102 has contaminated the space 104, or vice versa. In some cases, the disease tracking system 106 may identify the basic reproduction number (also referred to as R0 or "R naught") of the infectious agent or disease, which may indicate the transmissibility of the infectious agent or disease to from the first individual 102 to other individuals. In some cases, the disease tracking system 106 has prestored the basic reproduction number of the infectious agent or disease. If the infectious agent or disease has a relatively high basic reproduction number (e.g., with measles morbillivirus or measles), then the disease tracking system 106 may be more likely to indicate that the first individual 102 has contaminated the space 104, even if the dwell time of the first individual 102 is relatively low. In contrast, if the infectious agent or disease has a relatively low basic reproduction number (e.g., some forms of influenza A viruses), then the disease tracking system 106 may be less likely to indicate that the first individual 102 has contaminated the space 104. In some examples, the disease tracking system 106 may look up the type of the transmissibility and/or the basic reproduction number in a table, which may be stored by the disease tracking system 106.

According to various implementations, the disease tracking system 106 may determine that the first individual 102 has contaminated the space 104 with the infectious agent based on the presence of the first individual 102 in the space 104, the dwell time of the first individual 102 in the space, the efficacy of the hand washing performed by the first individual, whether the first individual 102 was wearing PPE in the space 104, and the type of infectious agent or disease that has infected the first individual 102. In some cases, the disease tracking system 106 may determine whether the first individual 102 has contaminated the space 104 based on the following Equation 1:

$$\alpha < f_{dwell}(t_{dwell})) * f_{wash}(e_{wash}) * f_{PPE}(p_{PPE}) * f_{rep}(R0) * f_{ex}(v_{ex})$$

wherein $\alpha$ represents a threshold (e.g., a constant), $f_{dwell}(t_{dwell})$ represents a function with respect to dwell time in the space 104, $f_{wash}(e_{wash})$ represents a function with respect to hand washing efficacy, $f_{PPE}(p_{PPE})$ represents a function with respect to whether the first individual 102 is wearing PPE, $f_{rep}(R0)$ represents a function with respect to the basic reproduction number of the infectious agent or disease, and $f_{ex}(v_{ex})$ represents a function with respect to the volume of the respired volume 112 exhaled by the first individual 102. In some examples, if the disease tracking system 106 determines that Equation 1 is true, then the disease tracking system 106 determines that the space 104 has been contaminated.

In some examples, the disease tracking system 106 may determine an exposure region within the space 104 based on a path that the first individual 102 follows through the space 104. The exposure region may include a boundary that is a particular distance from the path of the first individual 102. The distance, for example, is based on the type of infectious disease (e.g., an R0 of the infectious disease), the dwell time of the first individual 102 at a location along the path, a hand washing efficacy of the first individual 102, whether the first individual was wearing PPE, the volume of the respired volume 112, and the like. The boundary of the exposure region may change over time. For example, the boundary of the exposure region may move toward the path of the first individual 102 over time, representing the gradual dissipation and/or denaturation of the infectious agent left behind by the first individual 102. The disease tracking system 106 may determine that the exposure region is a region within the space 104 that has been contaminated.

The disease tracking system 106 may generate a contamination report 128 based on determining that the space 104 has been contaminated with the infectious agent. In some examples, the contamination report 128 includes a map that indicates the contaminated space 104. For instance, the map may indicate a geofenced region of the contaminated space 104 within a larger region, such as a building containing the contaminated space 104. In some cases, the contamination report 128 omits an identification (e.g., a name) of the first individual 102, thereby keeping the identity of the first individual 102 private from others.

The disease tracking system 106 may transmit the contamination report 128 to one or more devices. For example, a second individual 130 may be associated with a second device 132 and a third individual 134 may be associated with a third device 136. The disease tracking system 106 may transmit the contamination report 128 to the second device 132 and/or the third device 136. In some examples, the contamination report 128 may instruct the second individual 130 and/or the third individual 134 to avoid the contaminated space 104. In some cases, the second individual 130 and/or the third individual 134 may be responsible for maintenance and cleaning of the space 104. For instance, the second individual 130 and/or the third individual 134 may be janitors of a building including the space 104. In various cases, the contamination report 128 may instruct the second individual 130 and/or the third individual 134 to restrict access to and/or disinfect the space 104.

In some cases, the disease tracking system 106 can reduce the risk of exposure of the infectious agent to other individuals in the space 104 by controlling a heating, ventilation, and air conditioning (HVAC) system 137 associated with the space 104. The HVAC system 137 is configured to control a temperature of the space 104 and includes, for example, a heater, a heat pump, an air conditioner, or the like. In addition, the HVAC system 137 is configured to control airflow of the space 104 and includes, for instance, one or more fans that move air in the space 104. In various examples, the HVAC system 137 is controlled at least in part based on the airflow sensor(s) 110 and/or the temperature sensor(s) 114. For example, the HVAC system 137 may activate the fan(s) in response to a signal from the airflow sensor(s) 110 indicating that the ambient air within the space 104 is stagnant or has a temperature outside of a predetermined range. In some examples, the HVAC system 137 may activate the heater, heat pump, or air conditioner in response to a signal from the temperature sensor(s) 114 indicating that multiple individuals within the space 104 have surface temperatures outside of a predetermined range. In particular implementations, the disease tracking system 106 can transmit a signal to the HVAC system 137 in response to determining that the space 104 has been contaminated by the infectious agent. Based on the signal, the HVAC system 137 may at least temporarily activate the fan(s), heater, heat pump, or air conditioner, which may increase the airflow within the space 104. Accordingly, the disease tracking system 106 and the HVAC system 137 may at least partially dissipate the infectious agent within the space 104 and/or other spaces. The disease tracking system 106 may control the HVAC system 137 in other ways to prevent the spread of the infectious disease, some of which will be described below with reference to FIG. 4.

In various implementations, the disease tracking system 106 may be further configured to determine the possible exposure of the infectious disease or agent to other individuals, such as to the second individual 130 and/or the third individual 134. The disease tracking system 106 may identify the locations of the second individual 130 and the third individual 134 similarly to determining the location of the first individual 102. For example, the APs 118 may exchange wireless data with the second device 132 and/or the third device 136, determine the locations of the second device 132 and/or the third device 136, and indicate the locations in the sensor data 108. In some cases, the second individual 130 may carry or wear a second badge 138 and the third individual 134 may carry or wear a third badge 140. The second badge 138 and the third badge 140 may respectively include tags whose positions may be sensed by the RTLS sensors 120. The RTLS sensors 120 may indicate the locations of the second badge 138 and the third badge 140 in the sensor data 108. Accordingly, the disease tracking system 106 may be configured to identify the locations of the second individual 130 and the third individual 134 over time.

The disease tracking system 106 may determine whether the second individual 130 and/or the third individual 134 have been exposed to the infectious agent by determining whether the locations of the second individual 130 and/or the third individual 134 have been inside of the exposed space 104 and/or the exposure region. In some cases, the disease tracking system 106 determines that the second individual 130 has been in the contaminated space 104 and/or the exposure region and therefore concludes that the second individual 130 has been exposed to the infectious agent. In some implementations, the disease tracking system 106 may further consider the dwell time of the second individual 130 in the space 104 and/or exposure region. For example, the disease tracking system 106 may determine that the second individual 130 has been exposed based on determining that the dwell time of the second individual 130 in the space 104 and/or the exposure region has exceeded a threshold dwell time. In contrast, the disease tracking system 106 may determine that the third individual 134 has not been exposed (or is at a low risk for exposure) by determining that the third individual 134 has not been inside of the contaminated space 104 and/or exposure region.

In some examples, the disease tracking system 106 may determine whether the second individual 130 and/or the third individual 134 have been exposed to the infectious agent by determining whether the locations of the second individual 130 and/or the third individual 134 have been within a threshold distance of the location or path of the first individual 102. For example, the disease tracking system 106 may determine a distance 144 between the first individual 102 and the second individual 130 based on the locations of the first individual 102 and the second individual 130. The disease tracking system 106 may compare the distance 144 to a threshold distance (e.g., 0 meters (m), 1 m, 2 m, 3 m, 4 m, or 5 m). If the disease tracking system 106 determines that the distance 144 is less than the threshold distance, the disease tracking system 106 may conclude that the second individual 130 has been exposed to the infectious agent. According to some implementations, the disease tracking system 106 may generate an alert indicating that the first individual 102 and second individual 130 are violating a social distancing norm based on determining that the distance 144 is less than the threshold distance. The alert, for example, may be output to one or more computing devices, such as the first device 116, the second device 132, or the third device 136. In some cases, the disease tracking system 106 may identify the distance 144 between the locations of the first individual 102 and the second individual 130 at different times. For example, if the second individual 130 is located within the threshold distance of a previous path of the first individual 102, the second individual 130 may be exposed to the infectious disease (e.g., in droplets and/or aerosols left behind by the first individual 102), even if the first individual 102 and the second individual 130 are never within the threshold distance at the same time.

The disease tracking system 106 may generate an exposure report 142 that informs the second individual 130 of the potential exposure to the infectious disease or agent. In some examples, the exposure report 142 indicates the infectious disease or agent. The exposure report 142 may further instruct the second individual 130 to seek medical care (e.g., to get tested and/or treated for the infectious disease or agent). In some cases, the exposure report 142 instructs the second individual 130 to stay home and to avoid unnecessary contact with others. For instance, the exposure report 142 may instruct the second individual 130 to work remotely for a particular time period (e.g., two weeks) until the risk of the second individual 130 developing the infectious disease and/or exposing others to the infectious agent has passed. In some cases, the exposure report 142 omits an identification (e.g., a name) of the first individual 102, thereby keeping the identity of the first individual 102 private from the second individual 130.

In various examples, the disease tracking system 106 may store data at least temporarily in a health database 146. For instance, the disease tracking system 106 may store data indicative of the risk that the first individual 102 has contracted the infectious disease (e.g., based on the sensor data 108 from the airflow sensor(s) 110 and temperature sensor(s) 114 and/or data from the first device 116), data indicative of the risk that the first individual 102 has contaminated the space 104 (e.g., based on the sensor data 108 from the APs 118, the RTLS sensors 120, the hand washing sensor(s) 124, and the camera(s) 126), data indicative of the locations of the first individual 102, the second individual 130, and the third individual 134 (e.g., based on the sensor data 108 from the APs 118 and the RTLS sensors 120), and the like. In some examples, the health database 146 may store the data in such a way that the identities (e.g., names or other identifying information) of the first individual 102, the second individual 130, and the third individual 134 are hidden. For example, the health database 146 can store a table indexed by arbitrary identification numbers associated with the first individual 102, the second individual 130, and the third individual 134, which may reduce the risk that confidential health information of the first individual 102, the second individual 130, and the third individual 134 can be exposed. In some examples, the data is securely transmitted (e.g., using encryption), access to the health database 146 is logged, and the disease tracking system 106 is authenticated prior to accessing the data stored in the health database 146.

Although FIG. 1 depicts the disease tracking system 106, the airflow sensor(s) 110, the temperature sensor(s) 114, the APs 118, the RTLS sensors 120, the hand washing sensor(s) 124, the camera(s) 126, the HVAC system 137, and the health database 146 as separate entities, implementations are not so limited. For example, the disease tracking system 106, the airflow sensor(s) 110, the temperature sensor(s) 114, the APs 118, the RTLS sensors 120, the hand washing sensor(s) 124, the camera(s) 126, the HVAC system 137, and the health database 146 may be implemented by one or more devices, such as one or more computing devices. These device(s) may be located within the space 104, outside of the space 104, or a combination thereof. In some cases, the disease tracking system 106, the airflow sensor(s) 110, the temperature sensor(s) 114, the APs 118, the RTLS sensors 120, the hand washing sensor(s) 124, the camera(s) 126, the HVAC system 137, and the health database 146 are implemented over a distributed network (e.g., a mesh network) of devices.

Figure 2:
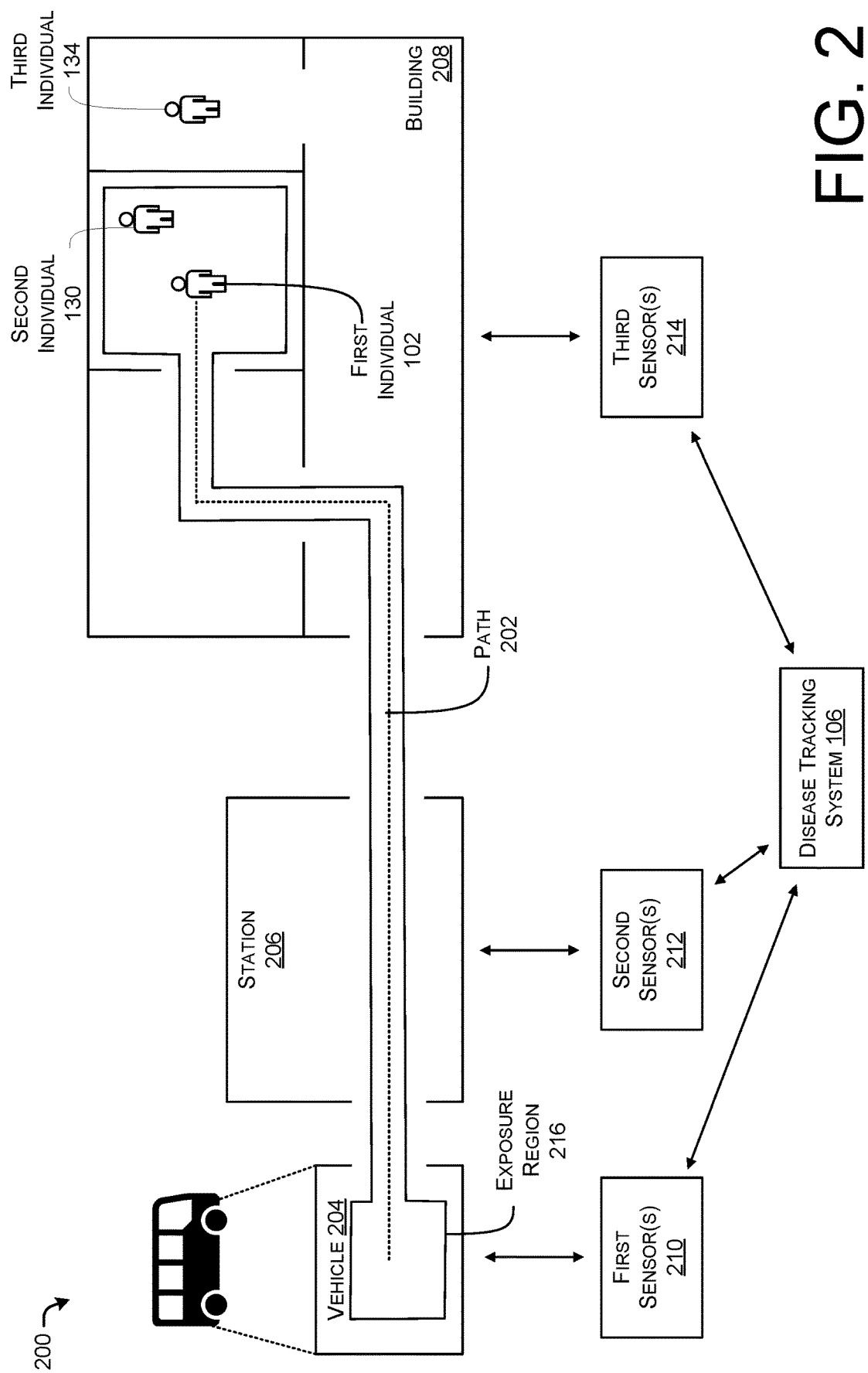
FIG. 2 illustrates an example environment of identifying the exposure of spaces and individuals to an infectious agent by an individual traveling through the spaces.

FIG. 2 illustrates an example environment 200 of identifying the exposure of spaces and individuals to an infectious agent by an individual traveling through the spaces. As shown, the environment 200 includes the first individual 102, the disease tracking system 106, the second individual 130, and the third individual 134 described above with reference to FIG. 1. As described above with reference to FIG. 1, the first individual 102 may have an infectious disease.

As shown in FIG. 2, the first individual 102 may travel along a path 202 that extends from a vehicle 204, to a station 206, and into a building 208. The space 104 described above with reference to FIG. 1 may be in the vehicle 204, the station 206, the building 208, or a combination thereof. In particular examples, the vehicle 204 may be a public bus on which the first individual 102 commutes to work, the station 206 may be a public bus terminal at which the vehicle 204 stops, and the building 208 may be a workplace of the first individual 102.

One or more first sensors 210 may be configured to monitor the vehicle 204, one or more second sensors 212 may be configured to monitor the station 206, and one or more third sensors 214 may be configured to monitor the building 208. The first sensor(s) 210, second sensor(s) 212, and third sensor(s) 214 may include at least one of the airflow sensor(s) 110, the temperature sensor(s) 114, the APs 118, the RTLS sensors 120, the hand washing sensor(s) 124, or the camera(s) 126 described above with reference to FIG. 1. For example, the first sensor(s) 210 and the second sensor(s) 212, which monitor public locations in the vehicle 204 and the station 206, may include one or more of the APs 118 configured to detect a position of a device associated with the first individual 102 as the first individual 102 is traveling along the path 202. In some instances, the third sensor(s) 214 include one or more of the APs 118 and/or the RTLS sensors 120, which may detect a position of the device associated with the first individual 102 and/or a badge of the first individual 102 when the first individual 102 is located in the building 208. Furthermore, the third sensor(s) 213 may be configured to detect the positions of devices and/or badges of the second individual 130 and/or the third individual 134 within the building 208. In various examples, the first sensor(s) 210, the second sensor(s) 212, and the third sensor(s) 214 are heterogenous. The first sensor(s) 210, the second sensor(s) 212, and the third sensor(s) 214 may be configured to transmit sensor data to the disease tracking system 106. The sensor data may be indicative of the locations of the first individual 102, the second individual 130, and the third individual 134 at different times.

In various examples, the disease tracking system 106 identifies the path 202 of the first individual 102 based on the sensor data from the first sensor(s) 210, the second sensor(s) 212, and the third sensor(s) 214. In addition, the disease tracking system 106 may identify the locations of the second individual 130 and the third individual 134 based on the sensor data. Furthermore, the disease tracking system 106 may identify the dwell times of the first individual 102, the second individual 130, and the third individual 134 at various locations within the environment 200, based on the sensor data. For example, the disease tracking system 106 may determine that the first individual 102 had a dwell time of 30 minutes within the vehicle 204, a dwell time of two hours within a room of the building 208, and minimal dwell times (e.g., less than five minutes) at other locations along the path 202.

The disease tracking system 106 may determine an exposure region 216 associated with the path 202 of the first individual based on the sensor data. The exposure region 216 may represent a volume or area of one or more spaces that have been contaminated by the infectious agent carried by the first individual 102. The exposure region 216 may correspond to a volume or area that the disease tracking system 106 warns individuals to avoid (e.g., in a contamination report) in order to reduce the risk that the individuals will contract the infectious agent. The exposure region 216, in some cases, corresponds to a volume or area that the disease tracking system 106 may instruct one or more individuals (e.g., janitors) to disinfect. In some cases, the exposure region 216 may correspond to a volume or area that, when crossed by an individual (e.g., the second individual 130), the disease tracking system 106 will notify the individual that they have been exposed to the infectious agent.

According to some examples, the exposure region 216 includes the path 202. The disease tracking system 106 may adjust the boundary of the exposure region 216 based on the dwell times of the first individual 102 at different locations along the path 202. For example, the boundary of the exposure region 216 within the vehicle 204 may be located at least a first distance (e.g., 10 feet) from the path 202, wherein the first distance is selected based on the 30 minute dwell time of the first individual 102 within the vehicle 204. The boundary of the exposure region 216 within the station 206 may be at least a second distance (e.g., 5 feet) from the path 202, wherein the second distance is selected based on the minimal dwell time of the first individual 102 within the station 206. Further, the boundary of the exposure region 216 within the building 208 may be at least a third distance (e.g., 20 feet) from the path 202, wherein the third distance is selected based on the 2 hour dwell time of the first individual 102 within the room of the building 208.

In various implementations, the disease tracking system 106 may adjust the boundary of the exposure region 216 based on physical structures proximate to the path 202. For example, the disease tracking system 106 may identify (e.g., based on a map) walls or other structures in the vehicle 204, the station 206, and the building 208. The infectious agent may be assumed to not cross the walls or other structures in the vehicle 204, the station 206, or the building 208. Thus, in some cases, the disease tracking system 106 may identify that the boundary of the exposure region 216 is a distance from the path 202 that does not pass through the walls or other structures. For example, a wall may be within the 20 feet from the path 202 within the room of the building 208, such that the boundary of the exposure region 216 is co-located with the wall. Various physical structures, such as walls, can be identified by the disease tracking system 106 via a map of the corresponding space (e.g., the vehicle 204, the station 206, and/or the building 208). The map may be predetermined or may be generated, by the disease tracking system 106, based on sensor data indicating the physical structures. For instance, the disease tracking system 106 may generate the map based on images of the space.

In some cases, the disease tracking system 106 may adjust the boundary of the exposure region 216 based on respiratory events of the first individual 102 along the path. For example, if the disease tracking system 106 detects that the first individual 102 has sneezed or coughed along the path 202, the disease tracking system 106 may expand the boundary of the exposure region 216. Similarly, the disease tracking system 106 may adjust the boundary of the exposure region 216 based on whether the first individual 102 has washed hands effectively, the ventilation efficacy in the area of the path 202 (e.g., whether the area is outside or indoors), and so on.

According to some examples, the boundary of the exposure region 216 may change over time. For example, the boundary of the exposure region 216 may shift toward the path 202 over time. In some cases, the boundary of the exposure region 216 may shift toward a location on the path 202 at a particular speed after the first individual 102 has moved away from the location. This shift may be used to model dissipation of aerosols and/or droplets over time and/or the degradation (e.g., denaturation) of the infectious agent within the ambient environment over time.

The disease tracking system 106 may determine whether individuals are exposed to the infectious agent by determining whether the individuals are located or have been located in the exposure region 216. For example, the disease tracking system 106 may determine, based on the sensor data, that the second individual 130 is located in the exposure region 216 and that the third individual 134 is located outside of the exposure region 216. The disease tracking system 106 may inform (e.g., via an exposure report) the second individual 130 of the exposure to the infectious agent.

In some implementations, the disease tracking system 106 may proactively send messages to devices proximate to the path 202, thereby warning individuals of possible exposures to the infectious agent. For example, the disease tracking system 106 may determine, based on sensor data from the second sensor(s) 212, that the infected first individual 102 is traveling through the station 206. The disease tracking system 106 may automatically alert individuals in the station 206 that they may be exposed to the infectious disease. For instance, the disease tracking system 106 may automatically push exposure reports to devices in the station 206 while the first individual 102 is in the station 206 or after the first individual 102 has been in the station 206. The disease tracking system 106 may identify the path 202 of the first individual 102, and pro-actively transmit exposure reports to devices proximate to the path 202, even as the path 202 intersects public spaces such as ambulances, transit stations, buses, trains, and the like, by pushing the exposure reports to APs (e.g., public WI-FI APs, 3GPP RANs, etc.) located in those public spaces. The APs, in turn, may transmit the exposure reports to devices within their respective coverage areas.

Figure 3:
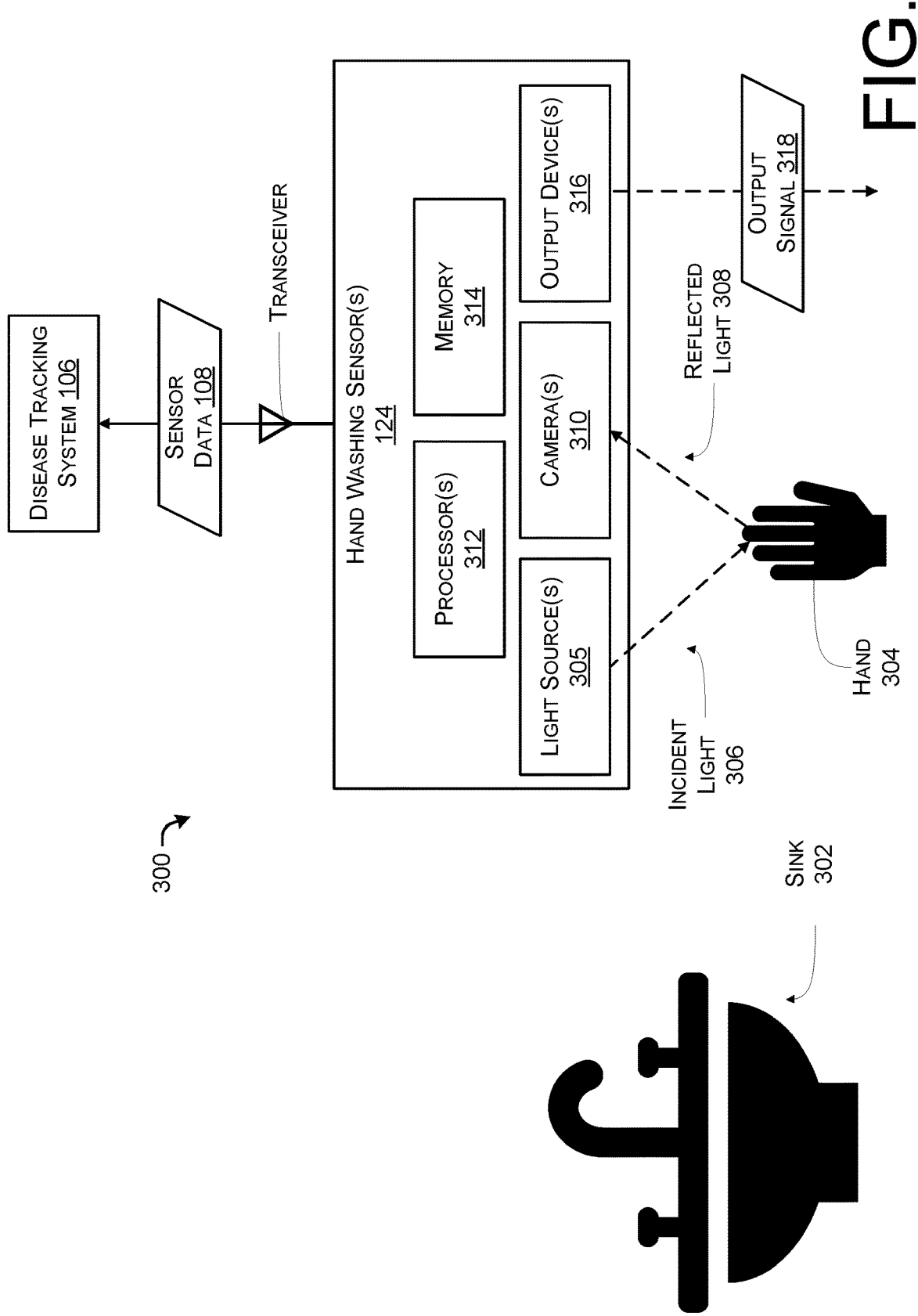
FIG. 3 illustrates an example of an environment that can be used to enhance hand washing efficacy and prevent the spread of an infectious disease.

FIG. 3 illustrates an example of an environment 300 that can be used to enhance hand washing efficacy and prevent the spread of an infectious disease. As shown, the environment 300 includes the disease tracking system 106, the sensor data 108, and the hand washing sensor(s) 124 described above with reference to FIG. 1.

In various implementations, the hand washing sensor(s) 124 may be positioned in the vicinity of a sink 302. For example, the hand washing sensor(s) 124 may be located within a particular distance (e.g., 3 feet, 5 feet, or 10 feet) of the sink 302. The hand washing sensor(s) 124 may be configured to monitor a hand 304 that has been washed by the sink 302. For example, the hand washing sensor(s) 124 may activate when the sink 302 is turned off.

The hand washing sensor(s) 124 may include one or more light sources 305. The one or more light source(s) 305 may, for example, include one or more light emitting diodes (LEDs), iridescent bulbs, or some other type of light source. The light source(s) 305 may be configured to transmit incident light 306 toward the hand 304. In particular cases, the incident light 306 includes ultraviolet (UV) light. The incident light 306 is reflected by the hand 304 as reflected light 308.

The hand washing sensor(s) 124 may include one or more cameras 310 configured to receive the reflected light 308. In various examples, the camera(s) 310 are configured to capture one or more images of the hand 304 that are indicative of the reflected light 308. The camera(s) 310 may be configured to generate digital data based on the image(s) of the hand 304.

In various cases, the hand washing sensor(s) 124 include one or more processors 312 and memory 314. The memory 314 may store instructions that, when executed by the processor(s) 312, causes the processor(s) 312 to perform operations including the data indicative of the image(s) captured by the camera(s) 310. For example, the processor(s) 312 may be configured to determine the presence of particles on the hand 304 based on the image(s) and/or the digital data. In some cases, the processor(s) 312 may be configured to determine an area of the surface of the hand 304 covered by the particles. In some cases, the processor(s) 312 may be configured to determine the amount of the particles on the hand 304. The particles may correspond to oils, dirt, dust, and other physical residue that can be removable from the hand 304 by effective hand washing. Thus, the presence of the particles, the area of the hand 304 covered by the particles, and the amount of the particles may be indicative of the efficacy of hand washing performed on the hand 304.

The hand washing sensor(s) 124 may further include one or more output devices 316. The output device(s) 316, for example, include a display screen, a light, a speaker, or the like. The output device(s) 316 may be configured to output an output signal 318 corresponding to the efficacy of the hand washing performed on the hand 304. For example, the processor(s) 312 may cause the output device(s) 316 to output an alert as the output signal 318 when the processor(s) 312 identify the presence of particles on the hand 304, that greater than a threshold percentage of the surface area of the hand 304 is covered in particles, that the amount of the particles on the hand 304 is greater than a threshold amount, or any combination thereof. The alert, for example, may include an instruction to rewash the hand 304. For instance, the output signal may be a visual signal (e.g., text on a screen, a blinking light, etc.), an audible signal, or a combination thereof. The alert may cause an individual to rewash the hand 304.

In some cases, the processor(s) 312 may determine that the hand 304 should be rewashed but has left a monitoring area of the hand washing sensor(s) 124 without being rewashed. For example, the hand 304 may be missing from a subsequent image captured by the camera(s) 310. Improper hand washing contributes to the spread of some infectious diseases. In various examples, the processor(s) 312 may generate at least a portion of the sensor data 108 indicating that the individual associated with the hand 304 is at a heightened risk for spreading an infectious disease. The processor(s) 312 may cause a transceiver 320 of the hand washing sensors) 124 to transmit the portion of the sensor data 108 to the disease tracking system 106.

In various examples, the disease tracking system 106 may identify the individual who the hand 304 belongs to using other forms of sensor data 108. For example, the disease tracking system 106 may receive sensor data 108 from one or more APs (e.g., the APs 118) and/or RTLS sensors (e.g., the RTLS sensors 120) indicating the location of the individual in an area captured by the camera(s) 310 when the hand 304 is captured. In various examples in which the individual is determined to have an infectious disease, the disease tracking system 106 may determine an exposure region individual based on the portion of the sensor data 108 received from the hand washing sensor(s) 124. For example, if the hand 304 is effectively washed, the exposure region may be narrower than an instance in which the hand 304 was not effectively washed.

Figure 4:
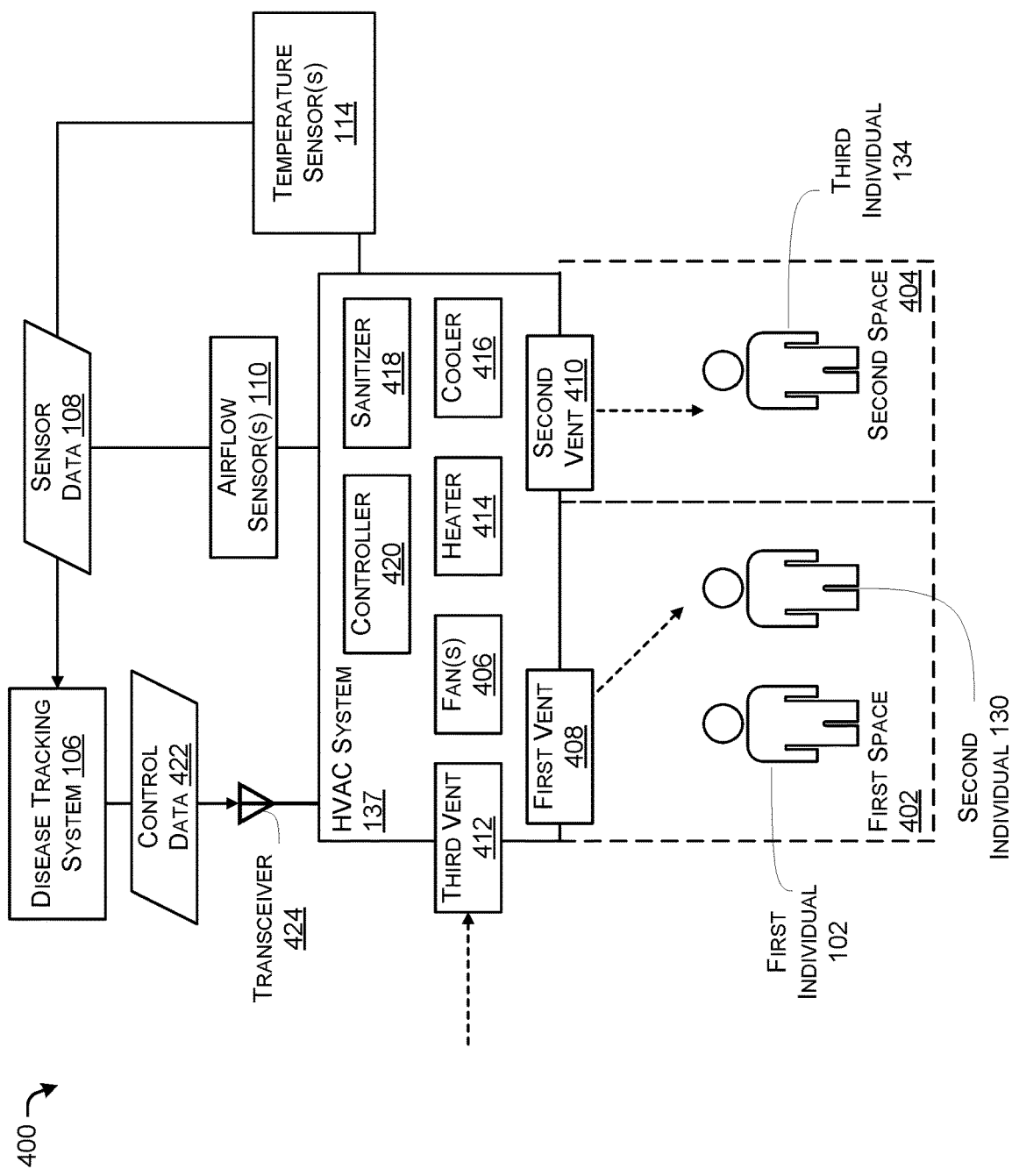
FIG. 4 illustrates an example of an environment for preventing the spread of an infectious disease in a building.
Figure 5:
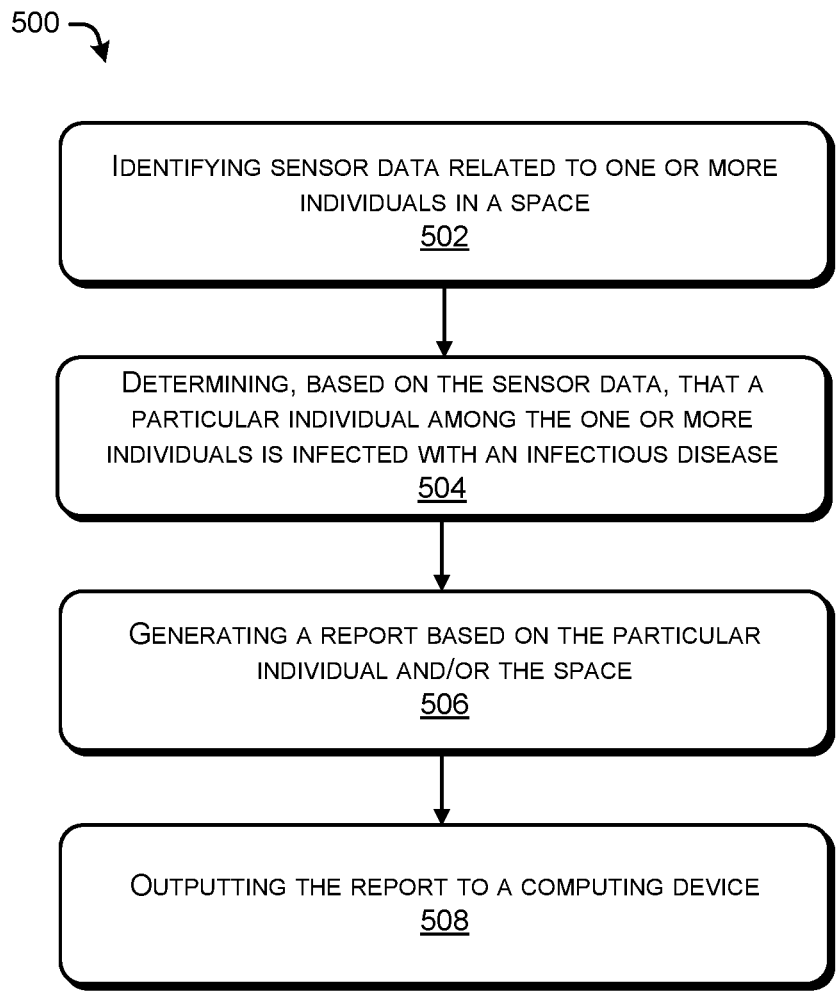
FIG. 5 illustrates an example process for identifying and reporting an individual with an infectious disease.
Figure 6:
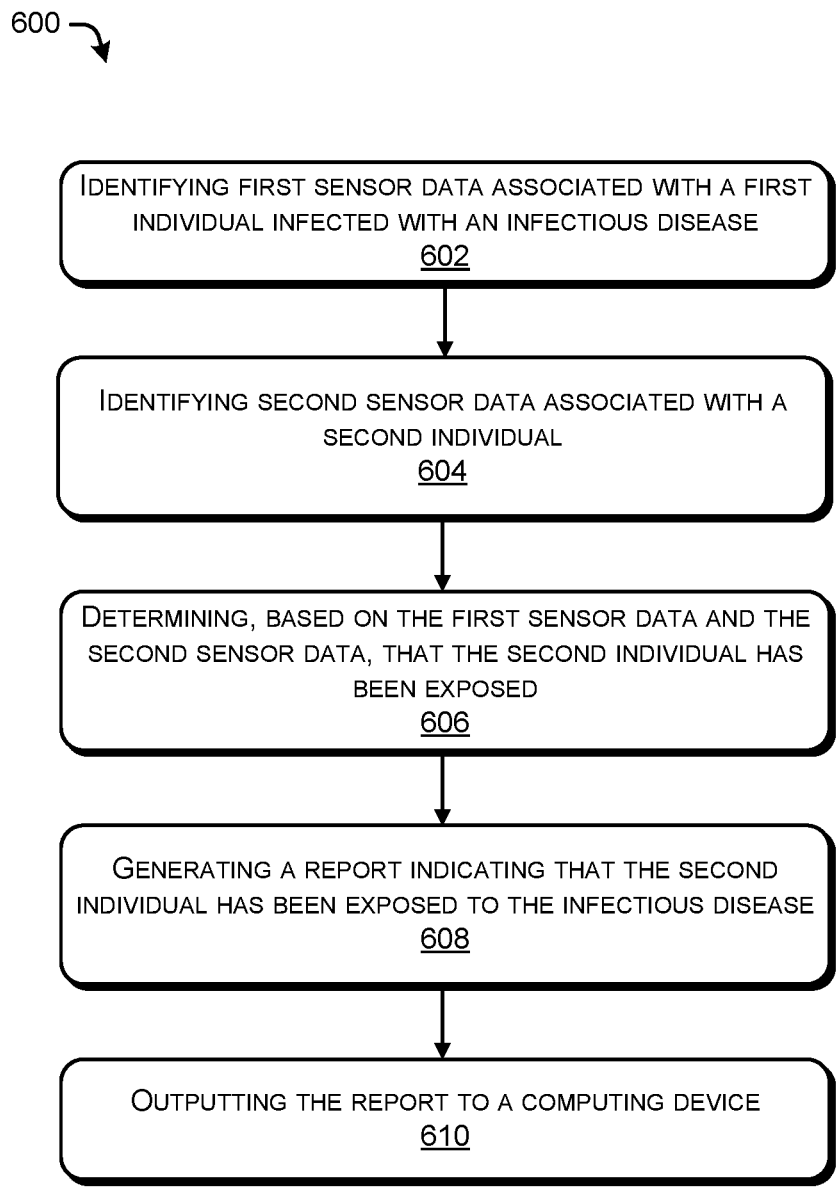
FIG. 6 illustrates an example process for reporting exposure of an infectious disease.

FIG. 4 illustrates an example of an environment 400 for preventing the spread of an infectious disease in a building. As shown, the environment 400 includes the first individual 102, the disease tracking system 106, the airflow sensor(s) 110, the temperature sensor(s) 114, the second individual 130, the third individual 134, and the HVAC system 137 described above with reference to FIG. 1.

In various implementations, the disease tracking system 106 may receive at least a portion of the sensor data 108 from the airflow sensor(s) 110 and/or the temperature sensor(s) 114. Based on the sensor data 108, the disease tracking system 106 may determine that the first individual 102 is infected with an infectious disease. The disease tracking system 106 may further determine that the infectious disease is transmissible through droplets or aerosols in the air.

To prevent the infectious disease from spreading to the second individual 130 and the third individual 134, the disease tracking system 106 may control the HVAC system 137. The HVAC system 137, for instance, may be configured to heat, ventilate, and cool air in a first space 402 and a second space 404. In particular, the HVAC system 137 may include one or more fans 406 configured to push air in and/or out of a number of vents, including a first vent 408, a second vent 410, and a third vent 412. In some examples, the first vent 408, the second vent 410, and the third vent 412 include one or more valves that, when closed, prevent air from flowing through one or more of the first vent 408, the second vent 410, or the third vent 412. In some cases, the first vent 408, the second vent 410, and the third vent 412 may include gratings and/or fans configured to direct the direction of the air flowing out of the first vent 408, the second vent 410, and/or the third vent 412.

The HVAC system 137 may further include a heater 414 and/or a cooler 416. The heater 414 may be configured to heat the air that is emitted through the vents. For example, the heater 414 may include a boiler, heat pump, radiator, or some other type of heating element. The cooler 416 may be configured to cool the air that is emitted through the vents. For example, the cooler 416 may include an air conditioner or heat pump.

The HVAC system 137 may also include a sanitizer 418 configured to at least partially disinfect air before it is emitted from the vents and/or filter contaminants from the air before it is emitted from the vents. In some examples, the sanitizer 418 includes a HEPA filter, a UV sanitizer, or the like.

In various examples, the HVAC system 137 includes a controller 420 that is communicatively coupled to various other elements within the HVAC system 137. The controller 420 may include one or more processors and memory storing instructions that, when executed by the processor(s), cause the processors to perform various operations. In addition, the controller 420 may include a digital to analog converter (DAC) configured to output analog signals to various elements within the HVAC system 137.

In particular examples, the HVAC system 137 may control the airflow through the first space 402 and the second space 404 based on signals from airflow sensor(s) 110 and/or temperature sensor(s) 114. For example, the controller 420 may activate the heater 414 if the temperature sensor(s) 114 indicate that an average surface and/or core temperature of various individuals within the first space 402 and/or the second space 404 is below a particular threshold.

As discussed above, the airflow sensor(s) 110 and/or temperature sensor(s) 114 may also transmit sensor data 108 to the disease tracking system 106. The disease tracking system 106 may determine that the first individual 102 is infected with an infectious disease based on the sensor data 108. Further, in some cases, the disease tracking system 106 may generate control data 422 based on the infectious disease of the first individual 102 and/or the location of the first individual. The disease tracking system 106 may transmit the control data 422 to the HVAC system 137. In particular, the HVAC system 137 may include a transceiver 424 configured to receive the control data 422 from the disease tracking system 106. For example, the control data 422 may be transmitted over one or more wireless networks.

The control data 422 may cause the HVAC system 137 to prevent the spread of the infectious disease from the first individual 102 to the second individual 130 or the third individual 134. The controller 420 may be configured to control the fan(s) 406, the first vent 408, the second vent 410, the third vent 412, the heater 414, the cooler 416, the sanitizer 418, or any combination thereof, based on the control data 422.

For example, based on the control data 422, the controller 420 may cause the first vent 408 associated with the first space 402 and/or the second vent 410 associated with the second space 404 to close. By closing the first vent 408, the HVAC system 137 may prevent aerosols and/or droplets from the first individual 102 in the first space 402 from spreading to the second space 404. Accordingly, the HVAC system 137 may prevent the second space 404 from being contaminated and/or the third individual 134 from being infected.

In some instances, based on the control data 422, the controller 420 may cause the first vent 408 to change a direction of air flowing into the first space 402. For example, the HVAC system 137 may increase an airflow around the second individual 130, which may prevent the second individual 130 from being exposed to a significant amount of aerosols and/or droplets from the first individual 102 in the first space 402. In some cases, the HVAC system 137 may prevent the airflow in the first space 402 from carrying aerosols and/or droplets from the first individual 102 to other regions of the first space 402 or to the second individual 130.

In some cases, based on the control data 422, the controller 420 may cause the fan(s) 406 to output an increased airflow to improve ventilation within the first space 402. The increased ventilation, in some examples, can decrease the chance that the infectious disease is spread from the first individual 102 to others (e.g., the second individual 130) in the first space 402.

In some examples, the infectious agent is sensitive to temperature. The control data 422 may cause the controller 420 to activate the heater 414 in order to increase the temperature of the airflow in the HVAC system 137 to a level above a threshold temperature (e.g., 30° C.) associated with destroying or otherwise deactivating the infectious agent. Alternatively, the control data 422 may cause the controller 420 to activate the cooler 416 in order to decrease the temperature of the airflow in the HVAC system 137 to a level below a threshold temperature (e.g., 30° C.) associated with maintaining dormancy of the infectious agent.

In some examples, the sanitizer 418 is selectively activated by the controller 420 based on the control data 422. For instance, the sanitizer 418, when active, may utilize a significant amount of electrical energy. Rather than activating the sanitizer 418 at all times, the sanitizer 418 may be deactivated to prevent energy expenditure by the HVAC system 137. In some cases, based on the control data 422, the controller 420 may activate the sanitizer 418. Accordingly, aerosols and/or droplets from the first space 402 may be sanitized before the air is recirculated into the first space 402 and/or the second space 404.

FIG. 5 illustrates an example process 500 for identifying and reporting an individual with an infectious disease. The process 500 may be performed by an entity, such as at least one of the disease tracking system 106, the airflow sensor(s) 110, the temperature sensor(s) 114, the health database 146, or any combination thereof, which are described above with reference to FIG. 1.

At 502, the entity may identify sensor data related to one or more individuals in a space. The sensor data, for example, is indicative of airflow in the space and/or temperatures of the one or more individuals in the space. In some examples, the sensor data is obtained by one or more IR cameras. The space may be an indoor space. The space may be, for example, an interior space of a vehicle (e.g., an ambulance, a bus, train, car, or the like), a hallway, an interior of a station (e.g., a bus station, a train station), a walkway, a room, an interior of a warehouse, or any combination thereof. In some examples, the space may include multiple rooms and/or hallways of the same building.

At 504, the entity may determine, based on the sensor data, that a particular individual among the one or more individuals is infected with an infectious disease. For example, the entity may determine, based on the sensor data, that the particular individual has coughed or sneezed greater than a threshold number of times. In various implementations, the entity may determine, based on the sensor data, that a respired volume of the particular individual is below a particular threshold volume. In some cases, the entity may determine, based on the sensor data, that a surface and/or body temperature of the particular individual is below a lower threshold temperature or above an upper threshold temperature.

At 506, the entity may generate a report based on the particular individual and/or the space. In some cases, the entity may generate a report that informs the particular individual that the particular individual has the infectious disease. For instance, the report my instruct the particular individual to self-quarantine (e.g., at home), to work remotely rather than entering a shared workspace, to seek medical treatment, or the like.

In various implementations, the entity may generate a report that indicates that the space is contaminated with an infectious agent associated with the infectious disease. In some cases, the entity determines that the space includes an exposure region of the particular individual. In some instances, the report instructs the other individual to sanitize and/or disinfect the space. In some cases, the report instructs the other individual to avoid the space (e.g., until it is disinfected). In various implementations, the report may refrain from exposing the identity of the particular individual and may instead identify the space.

At 508, the entity may output the report to a computing device. For example, the entity may transmit the report to the computing device over one or more communication networks. In various examples, the computing device is associated with the particular individual (e.g., in examples in which the report informs the particular individual of the infectious disease) or associated with the other individual (e.g., in examples in which the report instructs the other individual to sanitize, disinfect, or avoid the space).

FIG. 6 illustrates an example process 600 for reporting exposure of an infectious disease. The process 600 may be performed by an entity, such as at least one of the disease tracking system 106, the APs 118, the RTLS sensors 120, the hand washing sensor(s) 124, the camera(s) 126, the health database 146, or any combination thereof, which are described above with reference to FIG. 1.

At 602, the entity may identify first sensor data associated with a first individual. The first individual may be infected with an infectious disease. In various examples, the first sensor data may indicate a location of the first individual over time (e.g., at one or more first times). For example, the first sensor data may indicate a location of a computing device (e.g., a mobile phone carried by the first individual, a laptop, a wearable device worn by the first individual or the like) associated with the first individual. The location of the first individual may be stationary, moving, or both throughout a space, such as a building, walkway, or interior of a vehicle.

At 604, the entity may identify second sensor data associated with a second individual. The second sensor data may identify the location of the second individual over time (e.g., at one or more second times). The second time(s) may be simultaneous with and/or subsequent to the first time(s). In some cases, the second sensor data may identify the location of a computing device (e.g., a mobile phone carried by the second individual, a laptop, a wearable device worn by the second individual or the like) associated with the second individual. The location of the second individual may be stationary, moving, or both throughout the space.

At 606, the entity may determine, based on the first sensor data and the second sensor data, that the second individual has been exposed to the infectious disease. In various examples, the entity may determine, based on the first sensor data and the second sensor data, that the location of the first individual and the location of the second individual were within a threshold distance (e.g., one meter, two meters, three meters, four meters, etc.) of one another. For example, the entity may determine that the location of the first individual and the second individual were within the threshold distance of one another without a physical structure (e.g., a wall) being disposed between the first individual and the second individual. That is, the first individual and the second individual may have had a clear line-of-sight with one another. For instance, the entity may identify whether the physical structure is present by comparing the location of the first individual and the location of the second individual to a map of the space in which the first individual and the second individual are located. According to some examples, the entity may determine that the location of the second individual is within the threshold distance of a path of the first individual. For example, the entity may determine that the location of the first individual and the second individual were within the threshold distance of one another without a physical structure (e.g., a wall) being disposed between the first individual and the second individual. That is, the first individual and the second individual may have been In some cases, the entity may determine that the first individual and the second individual were within the threshold distance for greater than a threshold dwell time (e.g., one second, thirty seconds, one minute, five minutes, ten minutes, thirty minutes, one hour, etc.).

According to some examples, the first sensor data may indicate that the first individual has sneezed or coughed. For example, the first sensor data may include data generated by one or more airflow sensors (e.g., the airflow sensor(s) 110) indicative of a sneeze or cough emitted by the first individual. In some cases, the entity may determine that the second individual has been exposed to the infectious disease by determining that the first individual has sneezed or coughed within a threshold distance (e.g., one meter, two meters, three meters, four meters, etc.) of the location of the second individual.

In various implementations, the entity may determine an exposure region of the first individual. For example, the entity may determine a boundary of the exposure region based on the path of the first individual, the times at which the first individual was detected at various locations along the path, the type of infectious disease that the first individual is exhibiting, a hand washing efficacy of the first individual, coughing and/or sneezing events by the first individual detected along the path, the map of the space, or a combination thereof. In some examples, the entity may adjust the boundary of the exposure region over time. For example, the exposure region may move at a velocity toward the path of the first individual. The entity, in various cases, may determine that the second individual has been exposed to the first individual by determining that the location of the second individual is or was within the exposure region of the first individual. In some cases, the entity may determine that the second individual has been within the exposure region for greater than a threshold dwell time.

At 608, the entity may generate a report indicating that the second individual has been exposed to the infectious disease. In some cases, the report may instruct the second individual to seek medical attention. In various cases, the report may instruct the second individual to self-quarantine (e.g., at home) or to otherwise avoid a public space (e.g., a public workplace). In various examples, the report may omit identifying information (e.g., a name) about the first individual.

At 610, the entity may output the report to a computing device. The computing device, for example, may be associated with the second individual. For example, the computing device may be a mobile device (e.g., a smartphone) associated with the second individual.

Figure 7:
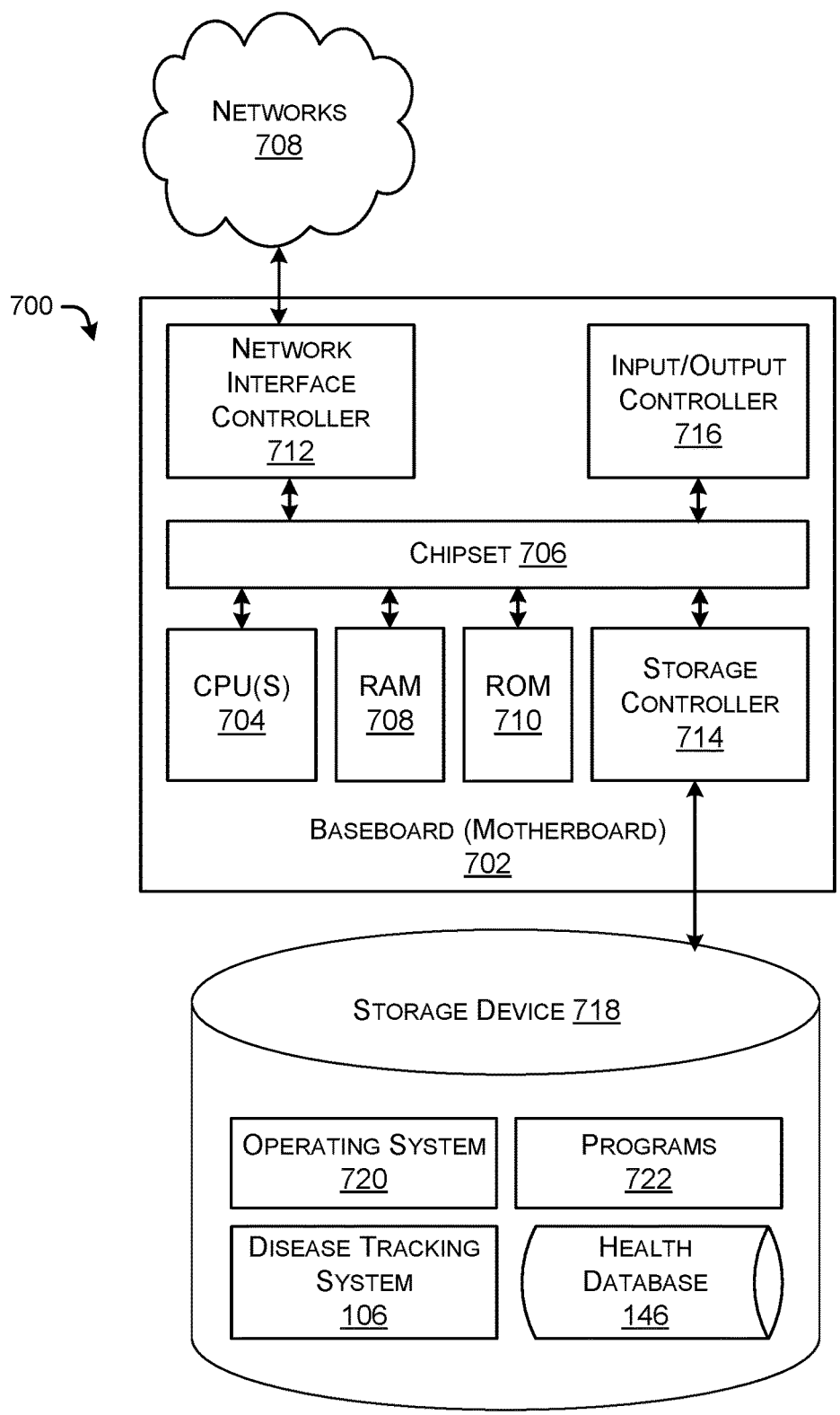
FIG. 7 shows an example computer architecture for a server computer capable of executing program components for implementing the functionality described herein.

FIG. 7 shows an example computer architecture for a server computer 700 capable of executing program components for implementing the functionality described above. The computer architecture shown in FIG. 7 illustrates a conventional server computer, workstation, desktop computer, laptop, tablet, network appliance, e-reader, smartphone, or other computing device, and can be utilized to execute any of the software components presented herein.

The computer 700 includes a baseboard 702, or "motherboard," which is a printed circuit board to which a multitude of components or devices can be connected by way of a system bus or other electrical communication paths. In one illustrative configuration, one or more central processing units ("CPUs") 704 operate in conjunction with a chipset 706. The CPUs 704 can be standard programmable processors that perform arithmetic and logical operations necessary for the operation of the computer 700.

The CPUs 704 perform operations by transitioning from one discrete, physical state to the next through the manipulation of switching elements that differentiate between and change these states. Switching elements generally include electronic circuits that maintain one of two binary states, such as flip-flops, and electronic circuits that provide an output state based on the logical combination of the states of one or more other switching elements, such as logic gates. These basic switching elements can be combined to create more complex logic circuits, including registers, adders-subtractors, arithmetic logic units, floating-point units, and the like.

The chipset 706 provides an interface between the CPUs 704 and the remainder of the components and devices on the baseboard 702. The chipset 706 can provide an interface to a random-access memory (RAM) 708, used as the main memory in the computer 700. The chipset 706 can further provide an interface to a computer-readable storage medium such as a read-only memory (ROM) 710 or non-volatile RAM (NVRAM) for storing basic routines that help to startup the computer 700 and to transfer information between the various components and devices. The ROM 710 or NVRAM can also store other software components necessary for the operation of the computer 700 in accordance with the configurations described herein.

The computer 700 can operate in a networked environment using logical connections to remote computing devices and computer systems through a network, such as the network 712. The chipset 706 can include functionality for providing network connectivity through a network interface controller (NIC) 712, such as a gigabit Ethernet adapter. The NIC 714 is capable of connecting the computer 700 to other computing devices over the network 712. It should be appreciated that multiple NICs 712 can be present in the computer 700, connecting the computer 700 to other types of networks and remote computer systems. In some instances, the NICs 712 may include at least on ingress port and/or at least one egress port.

The computer 700 can be connected to a storage device 718 that provides non-volatile storage for the computer. The storage device 718 can store an operating system 720, programs 722, and data, which have been described in greater detail herein. The storage device 718 can be connected to the computer 700 through a storage controller 714 connected to the chipset 706. The storage device 718 can consist of one or more physical storage units. The storage controller 714 can interface with the physical storage units through a serial attached small (SAS) computer system interface (SCSI) interface, a serial advanced technology attachment (SATA) interface, a fiber channel (FC) interface, or other type of interface for physically connecting and transferring data between computers and physical storage units.

The computer 700 can store data on the storage device 718 by transforming the physical state of the physical storage units to reflect the information being stored. The specific transformation of physical state can depend on various factors, in different embodiments of this description. Examples of such factors can include, but are not limited to, the technology used to implement the physical storage units, whether the storage device 718 is characterized as primary or secondary storage, and the like.

For example, the computer 700 can store information to the storage device 718 by issuing instructions through the storage controller 714 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 700 can further read information from the storage device 718 by detecting the physical states or characteristics of one or more particular locations within the physical storage units.

In addition to the mass storage device 718 described above, the computer 700 can have access to other computer-readable storage media to store and retrieve information, such as program modules, data structures, or other data. It should be appreciated by those skilled in the art that computer-readable storage media is any available media that provides for the non-transitory storage of data and that can be accessed by the computer 700. In some examples, the operations performed by any network node described herein may be supported by one or more devices similar to computer 700. Stated otherwise, some or all of the operations performed by a network node may be performed by one or more computer devices 700 operating in a cloud-based arrangement.

By way of example, and not limitation, computer-readable storage media can include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

As mentioned briefly above, the storage device 718 can store an operating system 720 utilized to control the operation of the computer 700. According to one embodiment, the operating system comprises the LINUX™ operating system. According to another embodiment, the operating system includes the WINDOWS™ SERVER operating system from MICROSOFT Corporation of Redmond, Washington. According to further embodiments, the operating system can comprise the UNIX™ operating system or one of its variants. It should be appreciated that other operating systems can also be utilized. The storage device 718 can store other system or application programs and data utilized by the computer 700.

In one embodiment, the storage device 718 or other computer-readable storage media is encoded with computer-executable instructions which, when loaded into the computer 700, transform the computer from a general-purpose computing system into a special-purpose computer capable of implementing the embodiments described herein. These computer-executable instructions transform the computer 700 by specifying how the CPUs 704 transition between states, as described above. According to one embodiment, the computer 700 has access to computer-readable storage media storing computer-executable instructions which, when executed by the computer 700, perform the various processes described above with regard to FIGS. 1-6. The computer 700 can also include computer-readable storage media having instructions stored thereupon for performing any of the other computer-implemented operations described herein.

As illustrated in FIG. 7, the storage device 718 stores programs 722 as well as the disease tracking system 106 and the health database 146. The programs 722, the disease tracking system 106, the health database 146, or any combination thereof, may include one or more instructions. The instructions, when executed by the CPU(s) 704, may cause the computer 700 and/or the CPU(s) 704 to perform one or more operations.

The computer 700 can also include one or more input/output controllers 716 for receiving and processing input from a number of input devices, such as a keyboard, a mouse, a touchpad, a touch screen, an electronic stylus, or other type of input device (e.g., any combination of the airflow sensor(s) 110, the temperature sensor(s) 114, the APs 118, the RTLS sensors 120, the hand washing sensor(s) 124, the camera(s) 126, the first sensor(s) 210, the second sensor(s) 212, or the third sensor(s) 214). Similarly, an input/output controller 728 can provide output to a display, such as a computer monitor, a flat-panel display, a digital projector, a printer, or other type of output device. It will be appreciated that the computer 700 might not include all of the components shown in FIG. 7, can include other components that are not explicitly shown in FIG. 7, or might utilize an architecture completely different than that shown in FIG. 6.

In some instances, one or more components may be referred to herein as "configured to," "configurable to," "operable/operative to," "adapted/adaptable," "able to," "conformable/conformed to," etc. Those skilled in the art will recognize that such terms (e.g., "configured to") can generally encompass active-state components and/or inactive-state components and/or standby-state components, unless context requires otherwise.

As used herein, the term "based on" can be used synonymously with "based, at least in part, on" and "based at least partly on." As used herein, the terms "comprises/comprising/comprised" and "includes/including/included," and their equivalents, can be used interchangeably. An apparatus, system, or method that "comprises A, B, and C" includes A, B, and C, but also can include other components (e.g., D) as well. That is, the apparatus, system, or method is not limited to components A, B, and C.

While the invention is described with respect to the specific examples, it is to be understood that the scope of the invention is not limited to these specific examples. Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Although the application describes embodiments having specific structural features and/or methodological acts, it is to be understood that the claims are not necessarily limited to the specific features or acts described. Rather, the specific features and acts are merely illustrative some embodiments that fall within the scope of the claims of the application.

What is claimed is:

1. A system, comprising
    a heating, ventilation, and air conditioning (HVAC) system comprising:
        one or more fans; and
        one or more vents;
    at least one processor;
    one or more infrared cameras configured to:
        detect a volume of air exhaled by a first individual based on a difference between a temperature of the volume of air exhaled by the first individual and an ambient temperature of ambient air in an enclosed space; and
        detect one or more vortices in the volume of air exhaled by the first individual; and
    one or more non-transitory media storing instructions that, when executed by the system, cause the system to perform operations comprising:
        identifying first sensor data indicative of a first badge associated with the first individual being at a first location for greater than a threshold time period;
        identifying second sensor data indicative of a second badge associated with a second individual being at a second location, the second location being within the enclosed space;
        determining that the first individual is infected with an infectious disease by determining that the first individual has coughed based on the one or more vortices in the volume of air;
        determining, based on the first sensor data and the second sensor data, that the first location was within a threshold distance of the second location;
        generating a report indicating that the second individual has been exposed to the infectious disease; and
        transmitting, to a computing device associated with the second individual, the report; and
            in response to determining that the first location was within the threshold distance of the second location: causing the one or more fans to increase a flow of air through the one or more vents and into the enclosed space; and
            causing the one or more vents to direct the flow of air toward the second location relative to the first location.

2. The system of claim 1, further comprising:
    a real time location system (RTLS) sensor configured to:
        generate the first sensor data by at least one of transmitting or receiving a first wireless signal with a first RTLS tag attached to the first badge; and
        generate the second sensor data by at least one of transmitting or receiving a second wireless signal with a second RTLS tag attached to the second badge.

3. The system of claim 1, further comprising:
    one or more infrared sensors configured to detect a temperature of the first individual,
    wherein determining that the first individual is infected with an infectious disease comprises determining that the temperature is greater than a threshold temperature.

4. The system of claim 1, further comprising:
    one or more infrared cameras configured to detect a volume of air inhaled or exhaled by the first individual,
    wherein determining that the first individual is infected with the infectious disease comprises determining that the volume of air is less than a threshold volume.

5. The system of claim 4, wherein determining, based on the first sensor data and the second sensor data, that the first location was within the threshold distance of the second location comprises determining, based on the volume of the air, that the first individual sneezed or coughed within the threshold distance of the second location.

6. The system of claim 1, the computing device being a first computing device,
    wherein the second sensor data is further indicative of a third location of the first computing device, and
    wherein the first sensor data is further indicative of third location of a second computing device associated with the first individual.

7. The system of claim 6, wherein the first sensor data comprises connectivity data indicative of one or more access points (APs) that have at least one of transmitted or received data wirelessly with the second computing device.

8. The system of claim 1, wherein the infectious disease comprises a viral infection, a fungal infection, a parasitic infection, or a bacterial infection.

9. The system of claim 1, the report being a first report, the computing device being a first computing device, the system further comprising:
    one or more real time location system (RTLS) sensors configured to generate the first sensor data by detecting the first badge at the first location and to generate the second sensor data by detecting the second badge at the second location;
    a noncontact temperature sensor configured to detect a temperature of the first individual; and
    a noncontact airflow sensor configured to detect a volume of air inhaled or exhaled by the first individual without contacting the first individual,
    wherein determining that the first individual is infected with the infectious disease is based on at least one of the temperature or the volume of the air,
    wherein determining that the first location was within the threshold distance of the second location comprises:
        determining that at least one of the first location was within the threshold distance of the second location for greater than a first threshold time period, or
        determining that the first location and the second location were simultaneously located in the enclosed space for greater than a second threshold time period, and
    wherein the operations further comprise:
        generating a second report indicating that the first individual is predicted to be infected with the infectious disease; and
        outputting, to a second computing device associated with the first individual, the first report.

10. The system of claim 1, the report being a first report, the computing device being a first computing device, wherein the operations further comprise:
    generating a second report requesting that a space comprising at least one of the first location or the second location be disinfected; and
    outputting, to a second computing device, the second report.

11. The system of claim 1, wherein the HVAC system further comprises:
    a heater, and
    wherein the operations further comprise:
        in response to determining that the first location was within the threshold distance of the second location, causing the heater to increase a temperature of the air above a threshold temperature associated with deactivating an infectious agent of the infectious disease or maintaining a dormancy of the infectious agent.

12. The system of claim 1, the enclosed space being a first enclosed space, the one or more vents being one or more first vents, the system further comprising:

one or more second vents disposed between the first enclosed space and a second enclosed space, a third individual being located in the second enclosed space, wherein the operations further comprise in response to determining that the first individual is infected with an infectious disease, preventing the flow of air from traveling into the second enclosed space by causing the one or more second vents to close.

13. The system of claim 1, wherein the one or more infrared cameras are further configured to detect a temperature of the first individual, and wherein determining that the first individual is infected with the infectious disease further comprises:

confirming that the first individual is infectious by determining that the temperature of the first individual is less than a first threshold or is greater than a second threshold, the first threshold and the second threshold being based on a time at which the temperature of the first individual is detected.

14. A system, comprising a heating, ventilation, and air conditioning (HVAC) system comprising:

one or more fans; and one or more vents;

one or more infrared cameras configured to:

detect a volume of air exhaled by a first individual based on a difference between a temperature of the volume of air exhaled by the first individual and an ambient temperature of ambient air in an enclosed space; and detect one or more vortices in the volume of air exhaled by the first individual;

at least one processor; and one or more non-transitory media storing instructions that, when executed by the system, cause the system to perform operations comprising:

identifying first sensor data indicative of a first badge associated with the first individual being at a first location for greater than a threshold time period;

identifying second sensor data indicative of a second badge associated with a second individual being at a second location, the second location being within the enclosed space;

determining that the first individual is infected with an infectious disease based on the one or more vortices;

determining, based on the first sensor data and the second sensor data, that the first location was within a threshold distance of the second location; and in response to determining that the first location was within the threshold distance of the second location:

causing the one or more fans to increase a flow of air through the one or more vents and into the enclosed space; and causing the one or more vents to direct the flow of air toward the second location.

* * * * *